United States Patent [19]

Slater et al.

[11] Patent Number: 4,971,671

[45] Date of Patent: Nov. 20, 1990

[54] PROCESSES FOR SEPARATION OF DNA FRAGMENTS

[75] Inventors: Gary W. Slater; Jaan Noolandi, both of Mississauga, Canada

[73] Assignee: Xerox Corporation, Stamford, Conn.

[21] Appl. No.: 20,401

[22] Filed: Mar. 2, 1987

[51] Int. Cl.[5] ...................... B01D 57/02; G01N 27/26

[52] U.S. Cl. ................................ 204/180.1; 204/182.8

[58] Field of Search .............. 204/182.7, 299 R, 180.1

[56] References Cited

U.S. PATENT DOCUMENTS 3,630,882 12/1971 Dilworth ............................ 204/299
3,870,612 3/1975 Flygare et al. ................ 204/180 R
3,930,982 1/1976 Batha et al. ........................ 204/299
4,061,561 12/1977 Fletcher et al. ................ 204/299 R
4,148,703 4/1979 Trop et al. ...................... 204/180 G
4,473,452 9/1984 Cantor et al. .................... 204/182.8
4,617,102 10/1986 Tomblin et al. ................ 204/299 R

OTHER PUBLICATIONS

"Pulsed-Field Gel Electrophoresis of Large DNA Molecules", by C. Smith and C. Cantor, Nature, vol. 319, Feb. 20, 1986, pp. 701-702.

"Molecular Karyotypes: Separating Chromosomes on Gels", by L. Corcoran, Bio Essays, vol. 3, No. 6, pp. 269-271.

"Electrophoretic Separation of Large DNA Molecules by Periodic Inversion of the Electric Field", by G. Carle, M, Frank, M. Olson, Science Reports, vol. 232, pp. 65-68.

"Separation of Chromosomal DNA Molecules from C. Albicans by Pulsed Field Gel Electrophoresis", Nucleic Acids Research, vol. 14, No. 11, pp. 4401-4406.

"Dependence of the Electrophoretic Mobility of DNA in Gels on Field, Intermittency", by T. Jamil, L. Lerman, Journal of Biomolecular Structure and Dynamics, vol. 2, Issue No. 5 (1985), pp. 963-966.

"Prediction of Chain Elongation in the Reptation Theory of DNA Gel Electrophoresis", by G. Slater, J. Noolandi, Biopolymers, vol. 24, No. 12, pp. 2181-2184.

"On the Reptation Theory of Gel Electrophoresis", by G. Slater, J. Noolandi, Biopolymers, vol. 25, pp. 431-454.

"New Biased-Reptation Model for Charged Polymers", by G. Slater, J. Noolandi, Physical Review Letters, vol. 55, No. 15, (1985), pp. 1579-1582.

"Fractionation of Large Mammalian DNA Restriction Fragments Using Vertical Pulsed-Field Gradient Gel Electrophoresis", by K. Gardiner, W. Laas, D. Patterson, Lomatic Cell and Molecular Genetics, vol. 12, No. 2, (1986), pp. 185-195.

"Mapping of the Class II Region of the Human Major Histocompatibility Complex by Pulsed-Field Gel Electrophoresis", by Hardy et al., Nature, vol. 323, (1986), pp. 453-455.

*Primary Examiner*—John F. Niebling
*Assistant Examiner*—Ben C. Hsing
*Attorney, Agent, or Firm*—Judith L. Byorick

[57] ABSTRACT

A process for enabling the separation of a mixture of DNA fragments comprising (1) providing an electrophoresis devive; (2) adding to the device a solution mixture containing DNA fragments of different lengths; (3) energizing the device, thereby creating a sequence of unidirectional uniform electric field pulses therein, said sequence of field pulses alternating between primary positive voltage pulses and secondary pulses of a negative or a positive polarity with less voltage than the primary pulses; (4) calculating the time duration and the field strength required for the primary and secondary field pulses to enable resolution of the fragments into separate and distinct groups corresponding their lengths; and (5) applying in the device the selected primary and secondary fields with intensities and durations corresponding to the size of fragments to be separated. Another embodiment of the invention comprises a computer program that facilitates a DNA gel electrophoresis process.

33 Claims, 10 Drawing Sheets

| FRAGMENT SIZE (Kilo Base Pairs) | $\tau_{str.}$ (Seconds) | $\tau_E$ (Seconds) | $\tau_D$ (Seconds) |
|---|---|---|---|
| 1 x 42 | 4.6 | 12 | 176 |
| 2 x 42 | 9.0 | 35 | 1416 |
| 3 x 42 | 13.6 | 65 | - - - |
| 4 x 42 | 18.0 | 99 | - - - |
| 5 x 42 | 22.8 | 139 | - - - |
| 10 x 42 | 46.0 | 396 | - - - |
| 20 x 42 | 90.0 | - - - | - - - |

| FRAGMENT SIZE (Kilo Base Pairs) | $\tau_{str.}$ (Seconds) | $\tau_E$ (Seconds) | $\tau_D$ (Seconds) |
|---|---|---|---|
| 1 x 42 | 4.6 | 12 | 176 |
| 2 x 42 | 9.0 | 35 | 1416 |
| 3 x 42 | 13.6 | 65 | - - - |
| 4 x 42 | 18.0 | 99 | - - - |
| 5 x 42 | 22.8 | 139 | - - - |
| 10 x 42 | 46.0 | 396 | - - - |
| 20 x 42 | 90.0 | - - - | - - - |

FIG. 1

| FRAGMENT SIZE (x 42 kbp) | 1 | 2 | 3 | 4 | 5 | 6 | >6 |
|---|---|---|---|---|---|---|---|
| DISTANCE / 75 Hours (mm) | 37 | 31 | 28 | 26 | 24 | 22 | <24 |

FIG. 2

| 1 and 2 (Kilo Base Pairs) | $\tau_{str.}$ (2 V/cm) (Seconds) | $\tau_E$ (2 V/cm) (Seconds) | $\tau_{str.}$ (-1 V/cm) (Seconds) | $\tau_{E.}$ (-1 V/cm) (Seconds) |
|---|---|---|---|---|
| 300 | 18 | 274 | 74 | 549 |
| 1000 | 61 | 1672 | 244 | 3346 |

*FIG. 3*

| Type of DNA and Sample No. | Multimers E-1 | Yeast Chromosomes YC-1 to YC-3 | Multimers C-1d,c |
|---|---|---|---|
| Series No. | 1 and 2 | 3 to 8 | 9 to 12 |
| Number of Bands Separated | 10 bands (42-420 kb) | 8 | 10 Bands (42-420 kb) |

*FIG. 4*

| FRAGMENT SIZE (x 42 kbp) | 1 | 2 | 3 | 4 | 5 | 6 | 7 |
|---|---|---|---|---|---|---|---|
| DISTANCE / 115 Hours (mm) | 37 | 31 | 28 | 26 | 24 | 22 | 20 |

| FRAGMENT SIZE (x 42 kbp) | 8 | 9 | 10 | - - | - - | - - | - - |
|---|---|---|---|---|---|---|---|
| DISTANCE / 115 Hours (mm) | 37 | 31 | 28 | - - | - - | - - | - - |

*FIG. 5*

PROCESSES FOR SEPARATION OF DNA FRAGMENTS

BACKGROUND OF THE INVENTION

The present invention is directed to a process for the separation and purification of DNA, and, more specifically, to processes for the separation of the chromosome fragments thereof. In one embodiment of the present invention, a process is provided for separating DNA fragments of any size. In another embodiment of the present invention, a process is provided which comprises providing a mixture of DNA fragments of desired sizes, depositing the fragments in a conventional gel electrophoresis apparatus, and applying a series of unidirectional field pulses across the gel, thereby enabling separation of the fragments according to their sizes. Another embodiment of the invention comprises the selection of a computer program that simulates a DNA gel electrophoresis process.

In the field of genetic engineering, DNA is typically studied by severing long DNA chains into smaller fragments using a restriction enzyme. The resulting fragments, which must then be separated according to size or composition, provide the information needed to construct a map of the original DNA chain. Construction of such a map is facilitated by severing the original DNA chain into a relatively small number of long fragments (preferably less than one hundred), as opposed to generating many short fragments. Also, as the number of pieces decreases, it becomes easier to reconstruct the original molecule. Conventional methods of fragment separation are limited in the mixtures containing fragments having more than 20,000 base pairs cannot readily or fully be separated. Therefore, with, for example the conventional methods of separation, it is required to cut human chromosomes into thousands of fragments to permit the separation thereof, thus reconstruction of the original chain would be extremely difficult.

In an attempt to alleviate some of these difficulties, variations on the standard known electrophoresis method have been developed. For example, there is described in U.S. Pat. No. 4,473,452, the disclosure of which is totally incorporated herein by reference, a pulsed field gradient gel electrophoresis method, which involves the application of two nonuniform electric fields positioned at approximately right angles to each other as a means of separating DNA fragments of over 20,000 base pairs. In addition, according to the abstract of the '452 patent, there is recited an apparatus for and a method of electrophoretically separating particles by electric fields which are approximately transverse to each other, and alternate between respectively high and low intensities out of phase with each other at a frequency related to the mass of the particles, thus permitting movement of the particles in an overall direction intermediate between the respective directions of the fields. In addition, this patent discloses the use of pulsed and crossed gradient electric fields to separate and resolve DNA fragments of up to several million base pairs. In contrast, with the process of the present invention, for example, several uniform fields are selected and applied in pulses in a single direction for the purpose of separating DNA fragments of any size.

Also, the '452 patent discloses that particularly good results are obtained when the on and off times of the alternate fields are proportional to the mass of the particles to be separated raised to a power of about 1.5. More specifically, this patent illustrates that the proper choice of a frequency at which the change from one field to another should occur is related to the time it takes the particle (molecule) of interest to orient itself into an elongated cylindrical shape, and that this time t is related to the mass of the particle (the molecular weight) M, the effective pore radius of the gel r, and the measured velocity of the particle in the gel v, in accordance with the relationship:

$$t \alpha M^{1.5}/(r^2 v)$$

Additionally, in the '452 patent it is indicated that variations on the invention, such as a differently shaped electrophoresis chamber, or differently produced, distributed or varied electric fields can be used provided that the particles are acted on by electric fields varying with time, permitting them to move in overall directions generally intermediate between at least two of the relevant, operationally significant fields. Moreover, more than two fields can be used providing the net effect is at least to act in the desired manner on a particle first in one direction, then in another direction transverse to the first, thereby moving the particle in a third direction intermediate between the first two. Thus, the process of the '452 patent requires the use of crossed alternating gradient fields to separate large DNA fragments.

The variation on standard electrophoresis process presented in the '452 patent is also discussed by C. L. Smith and C. R. Cantor in "Pulsed-Field Gel Electrophoresis of Large DNA Molecules," *Nature*, Vol. 319, pages 701–702 (1986), and by L. M. Corcoran in "Molecular Karyotypes: Separating Chromosomes on Gels," *BioEssays*, Vol. 3, No. 6, pages 269–271 (1985), the disclosure of each of these articles being totally incorporated herein by reference. Another modification of the standard electrophoresis method is disclosed by G. F. Carle, M. Frank, and M. V. Olson in "Electrophoretic Separations of Large DNA Molecules by Periodic Inversion of the Electric Field," *Science Reports*, Vol. 232, pages 65–68 (1986), the disclosure of which is totally incorporated herein by reference. This article discloses a method for the separation of DNA fragments containing 15,000 to over 700,000 base pairs by periodically inverting a uniform electric field of a given strength in one dimension.

In an article by R. G. Snell and R. J. Wilkins entitled "Separation of Cromosomal DNA Molecules from *C. albicans* by Pulsed Field Gel Electrophoresis," *Nucleic Acids Research*, Vol. 14, No. 11, pages 4401–4406 (1986), the disclosure of which is totally incorporated herein by reference, the authors discuss the method of separation disclosed in the '452 patent. The article indicates that variations in experimental conditions such as pulse time, temperature, and relative voltage conditions have critical effects on the quality of results, and that pulsed field gel electrophoresis can be used to resolve DNA from chromosomes of the *Candida albicans* and *Saccharomyces cerrevisiae* strains of yeast. According to the aforementioned article, the single most important factor for obtaining optimal resolution was the elevation of the electrophoresis temperature to 35° C. Alteration of relative voltage conditions by 10 percent, pulse time by 20 percent, or temperature by 10 percent was, according to this article, found to destroy the electrophoretic pattern.

"Dependence of the Electrophoretic Mobility of DNA in Gels on Field Intermittency," T. Jamil and L. S. Lerman, Journal of *Biomolecular Structure and Dynamics*, Vol. 2, No. 5, pages 963–966 (1985), the disclosure of which is totally incorporated herein by reference, addresses the effect of varying pulse duration and varying the interval between pulses upon the mobility of DNA fragments in gels. This article illustrates the mobility of lambda DNA fragments containing from 3,400 to 21,800 base pairs when a single pulsed field is applied. The authors concluded that if the interval between pulses remains constant, the apparent mobility increases as the duration of pulses increases; however, it approaches a maximum. Additionally, this article discloses that when the pulse duration is constant, the apparent mobility decreases as the interval between pulses becomes longer. The changes in apparent mobility due to pulse duration and pulse interval are reported in this article to be relatively small for short fragments of 3,400 base pairs, and quite large for longer fragments of 10,000 base pairs and more. In addition, it is indicated in this article that the dependence of the mobility on pulse interval and duration decreases with decreasing ion concentration in the gel (the authors varied the sodium ion concentration between 0.04 to 0.4 M); and these effects become larger with decreasing pore size in agarose. Further, the article presents some mathematical analysis concerning the reasons for the observed greater effects on larger molecules, but provides no quantitative information related to DNA fragments containing more than 22,000 base pairs. Also, no mention is presented in this article relating to the mathematical analysis as a guide to a process for separating large DNA fragments by choosing optimal experimental conditions for a given mixture of fragments.

In "Prediction of Chain Elongation in the Reptation Theory of DNA Gel Electrophoresis," *Biopolymers*, Vol. 24, No. 12, pages 2181–2184 (1985), the disclosure of which is totally incorporated herein by reference, G. W. Slater and J. Noolandi provide a theoretical discussion of the reptation theory of DNA chain motion with respect to gel electrophoresis. This article discloses three time scales which are used in calculating optimal experimental conditions for the method of the present invention; it does not, however, provide a full quantitative analysis of the correlation between the time scales, the duration of applied field pulses, and the sizes of DNA fragments to be separated. A detailed quantitative analysis is provided in "On the Reptation Theory of Gel Electrophoresis," G. W. Slater and J. Noolandi, *Biopolymers*, Vol. 25, No. 3, pages 431–454 (Mar. 1986), the disclosure of which is totally incorporated herein by reference, and this analysis is important for the purpose of understanding and/or deriving a basis of the present invention.

Many references disclose the basic process of gel electrophoresis. For example, U.S. Pat. No. 3,630,882 teaches an apparatus for particle separation wherein a mixture of particles in a suspending medium is subjected to an intermittent DC electrical field of sufficient strength to produce a sharp separation of two or more components of the mixture. The electric field is intermittent or pulsed so that the particles in the material are alternately subjected to high electric field and low or zero electric field.

Also, U.S. Pat. No. 3,870,612 teaches a method of determining the electrophoretic mobility and diffusion coefficient of a macromolecular polymer in solution wherein the macromolecules are driven through the solution by an electric field in a modified electrophoretic cell. The electric field is pulsed, and the pulses are of alternating polarity to allow for the use of high fields and to prevent formation of concentration gradients.

Further, in U.S. Pat. No. 3,930,982 there is disclosed an apparatus for generating a periodic non-uniform electric field for the purpose of removing polarizable particulate material from a liquid by dielectrophoresis. The liquid containing particles to be removed is passed over a ferroelectric apparatus, which generates a periodic non-uniform electric field near the boundary between alternately polarized portions of the ferroelectric material, which periodic non-uniform electric field is generated by subjecting portions of the ferroelectric material to an alternating potential to alternately polarize the portions, while allowing other portions of the ferroelectric material to remain polarized in the same direction.

In addition, in U.S. Pat. No. 4,148,703 there is disclosed a method of electrophoretic purification of electrically charged biomolecules which uses different geometrically shaped electrode configurations, permitting potentially different gradients and enabling different particle velocities, finer separations, and continuous electrophoresis by means of a higher voltage in a smaller area, with a decrease in power expenditure. The various electrode systems are alternately turned on and off at a given time independently of one another and for a given duration of time; and in U.S. Pat. No. 3,506,554, there is illustrated a process and apparatus for separating electrophoretically active substances, such as proteins. The method utilizes a continuously flowing stream of buffer to transport the substances through a zone having an inert material that is pereable to either the electrophoretically active material or small buffer ions, such as a polyacrylamide gel slab. The process includes applying an electric field first in one direction and then in another direction to enable separation, and the cycle of reversing the direction of the electric field is repeated many times.

There is disclosed in U.S. Pat. No. 4,061,561 an electrophoresis apparatus that allows for high resolution by performing two dimensional migrations in a square tray. The sample selected is subjected to a linear current in one direction, and the tray is then turned exactly ninety degrees so that the first migration is pulled apart from an orthogonal direction. Also, the '561 patent discloses a multiple-sample applicator that allows an operator to deposit multiple samples on the gel or membrane either simultaneously or one at a time.

A process and apparatus for purifying and concentrating DNA from a crude DNA - containing mixture, such as whole blood, is disclosed in U.S. Pat. No. 4,617,102. The apparatus of the '102 patent consists essentially of an agarose gel disc immersed in an electrophoresis buffer solution and supported between two eight-micrometer polycarbonate filters in an electric field. Placing the sample on the disc and applying an electric field results in the separation of the DNA from the other components of the crude mixture. However, the reference does not, for example, teach a method of separating DNA particles of different molecular weights from each other.

Other references of interest include U.S. Pat. No. 4,322,275; "Fractionation of Large Mammalian DNA Restriction Fragments Using Vertical Pulsed - Field Gradient Gel Electrophoresis," K. Gardiner, W. Laas, and D. Patterson, *Somatic Cell and Molecular Genetics*, Vol. 12, No. 2, pages 185-195 (1986); "Mapping of the Class II Region of the Human Major Histocompatibility Complex by Pulsed - Field Gel Electrophoresis," D. A. Hardy et al., *Nature*, Vol. 323, pages 453-455 (1986); and "New Biased - Reptation Model for Charged Polymers," G. W. Slater and J. Noolandi, *Physical Review Letters*, Vol. 55. No. 15, pages 1579-1582 (1985).

Current methods used for separation of DNA fragments having more than 20,000 base pairs have several disadvantages. In some instances, commercially available electrophoresis equipment must be modified before these methods can be applied. For example, the process disclosed in the '452 patent involving the use of crossed gradient fields, requires extensive alterations to conventional gel electrophoresis apparatus. Also, all of the above described systems intended for separating DNA fragments of more than 20,000 base pairs use relatively high electric fields (above 3 volts/cm) necessitating the implementation of a bulky and expensive cooling system to avoid degradation of the gel and/or the DNA, whereas in one embodiment of the present invention the electric field may be as low as 0.25 volts/cm. In addition, no method currently known provides a reliable way of determining in advance the values of experimental parameters that must be selected to obtain optimal resolution of a given mixture of DNA fragments. Optimal resolution may be defined as obtaining results wherein most or all of the fragments of a particular size may be found in a distinct band that does not overlap with bands of fragments of another size on the termination of the process. Further, the existing methods of separation often lead to non-reproducible results, a disadvantage alleviated with the process of the present invention.

SUMMARY OF THE INVENTION

It is an object of the present invention to overcome some of the above noted disadvantages.

It is another object of the present invention to provide a process for separating DNA fragments of any size.

It is yet another object of the present invention to provide a method of separating large DNA fragments without the necessity of using crossed fields, which have the above noted disadvantages.

Additionally, it is another object of the present invention to provide a method of separating DNA fragments of over 20,000 base pairs with modified conventional, commercially available electrophoresis apparatuses.

Furthermore, it is another object of the present invention to provide a process wherein optimal resolution of mixtures of DNA fragments is effected by selecting optimal resolution of mixtures of DNA fragments is effected by selecting optimal experimental parameters.

It is yet another object of the present invention to provide a method of separating mixtures of DNA fragments with reproducible results.

In addition, it is still another object of the present invention to provide a computer program that simulates a DNA gel electrophoresis process, which program is useful for the process of the present invention.

These and other objects of the present invention are accomplished by the combination of known electrophoresis techniques and a new method of correlating the required field pulse characteristics and other process conditions with the size of the fragments to be resolved. Thus, in one embodiment of the present invention, a mixture of DNA particles is deposited in a conventional gel electrophoresis apparatus with a power supply and a single, uniform primary electric field having a positive voltage is applied in pulses in one direction. During the period between primary pulses, a secondary pulse of either a positive or a negative voltage is applied. Alternatively, during the period between primary pulses, secondary "pulses" of zero-field conditions may be applied. The aforementioned mixture of DNA fragments comprises, in one embodiment of the present invention, a solution or gel sample containing DNA fragments of at least two different sizes. For example, a mixture could contain fragments having 100,000; 200,000; 300,000; 400,000; and 500,000 base pairs. The durations of the primary and secondary pulses during the process are selected according to the formulae disclosed by G. W. Slater and J. Noolandi in "On the Reptation Theory of Gel Electrophoresis," *Biopolymers*, vol. 25, pages 431-454 (1986), the disclosure of which is totally incorporated herein by reference.

Although it is not desired to be limited by theory, it is believed that with the processes of the present invention three different characteristic times are associated with the stretching and the relaxation of the DNA fragments during pulsed field electrophoresis as follows:

A. "Characteristic stretching time" $\tau_{str.}$ is determined, in seconds, by $$\tau_{str.} = \frac{Qa^2}{2\,k_BT\,\mu_0}\left(\frac{qEa}{2k_BT}\right)^{-2}$$

B. "Relaxation time" $\tau_D$, in seconds, is determined by $$\tau_D = \frac{Q^3}{3\pi^2 k_BT\,\mu_0\,(q/a)^2}$$

C. "Full stretching time" $\tau_E$, in seconds, is determined by $$\tau_E = \sqrt{\pi/6}\cdot\frac{(Q/q)^{3/2}a}{E\,\mu_0}$$

where, for the above, $a$=average pore size in the gel (in meters)

q=average charge of DNA per pore (in coulombs)

Q=total charge of the DNA fragment (in coulombs)

E=electric field (in volt/meter)

$\mu_0$=free solution mobility of DNA in the buffer (in $m^2$/v sec.)

T=temperature (in °Kelvin)

$k_B$=Boltzmann constant=$1.38\times10^{-23}$ joule/°K $\pi\simeq3.1416$

For optimal results with the process of the present invention, the time duration of the primary pulses, during which the DNA fragments migrate in the forward direction and stretch at the same time, is chosen between the characteristic stretching time $\tau_{str.}$ and the full stretching time $\tau_E$ of the largest fragment to be separated in the DNA mixture. The time duration of the secondary pulse, during which the DNA fragments relax and either do not migrate (zero-field) or migrate backward (reverse field) or forward (secondary positive field), must be chosen between the characteristic stretching time $\tau_{str.}$ and the full stretching time $\tau_E$ of the largest fragment to be separated in the DNA mixture when a positive or negative secondary field is used to force fragment relaxation. When no field is used during the secondary pulses, the relaxation time $\tau_D$ represents the maximum time duration selected for these pulses. Also, to obtain reasonable mobilities for the fragments involved, the primary and secondary fields $E_p$ and $E_s$, and the primary and secondary pulse durations $T_p$ and $T_s$ should be selected such that $$\frac{E_p}{E_s} \quad \frac{T_s}{T_p}$$

Calculation of these times for the electric field(s) used for electrophoresis and the fragments to be separated provides the range of pulse durations selected for the process of the present invention. The equations for $\tau_{str.}$ and $\tau_D$ are detailed in G. W. Slater and J. Noolandi, "On the Reptation Theory of Gel Electrophoresis," *Biopolymers*, Vol. 25, pages 431–454 (1986), the disclosure of which is totally incorporated herein by reference; while the equation for $\tau_E$ can be derived from Equation (7) of the same paper. Typically, the primary pulse is applied for about ten seconds to about three hundred seconds, while the secondary pulse is applied for about ten seconds to about one thousand seconds.

The process of the present invention is useful for the separation of DNA fragments of varying sizes without resorting to crossed-field gel electrophoresis and its accompanying complications. Also, the process of the present invention eliminates the need to spend time determining optimal separation conditions experimentally, especially since ideal parameters can be provided as part of the process. In addition, the process of the present invention can be used to separate mixtures of fragments of any size. Theoretically, the sizes of fragments to be separated are unlimited; generally, however, fragments ranging in size of from about 2,000 base pairs to 2,500,000 base pairs can be resolved with the process of the present invention. Furthermore, the process of the present invention can be selected to obtain reproducible results permitting DNA fragments of a given size to be separated by the same sequence of field pulses in different commercially available gel electrophoresis cells when all other process conditions are retained. Moreover, with the present process research will be facilitated in areas such as separation of chromosomal DNA, chromosomal mapping, production of genetic libraries, and studies on the effects of various drugs on chromosomal DNA.

BRIEF DESCRIPTION OF THE DRAWINGS

For a better understanding of the present invention and its features, items such as computational results and experimental data have been presented in tabulated form. Also, for various preferred embodiments of the present invention, reference is made to the following figures, wherein:

FIG. 1 is a table with the results of calculations performed to determine estimated values of $\tau_{str.}$, $\tau_E$, and $\tau_D$ for the experimental conditions of Example I;

FIG. 2 is a table with the experimental results of Example I in terms of the distance traveled in the gel by each group of fragments present in the initial mixture;

FIG. 3 is a table with the results of calculations performed to determine estimated values of $\tau_{str.}$ and $\tau_E$ for the experimental conditions of Example II;

FIGS. 4 and 5 are tables with the experimental results of Example II in terms of the distance traveled in the gel by each group of fragments present in the initial mixture;

DESCRIPTION OF THE PREFERRED EMBODIMENTS

Figure 6A:
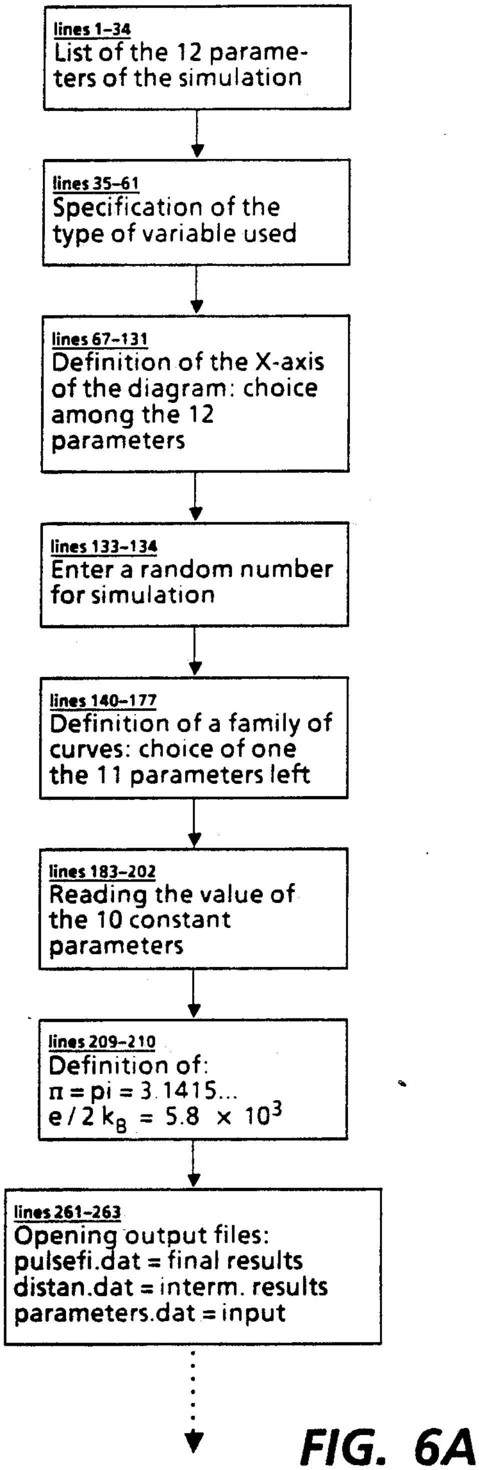
FIGS. 6A–6E is a flow chart for a computer program that simulates a pulsed field gel electrophoresis process and allows for the rapid calculations for the process of the present invention, thus permitting the determination of optimal process conditions for any separation to be performed with a high degree of precision, and to identify the various bands of fragments present in the gel at the end of an experiment.
Figure 6B:
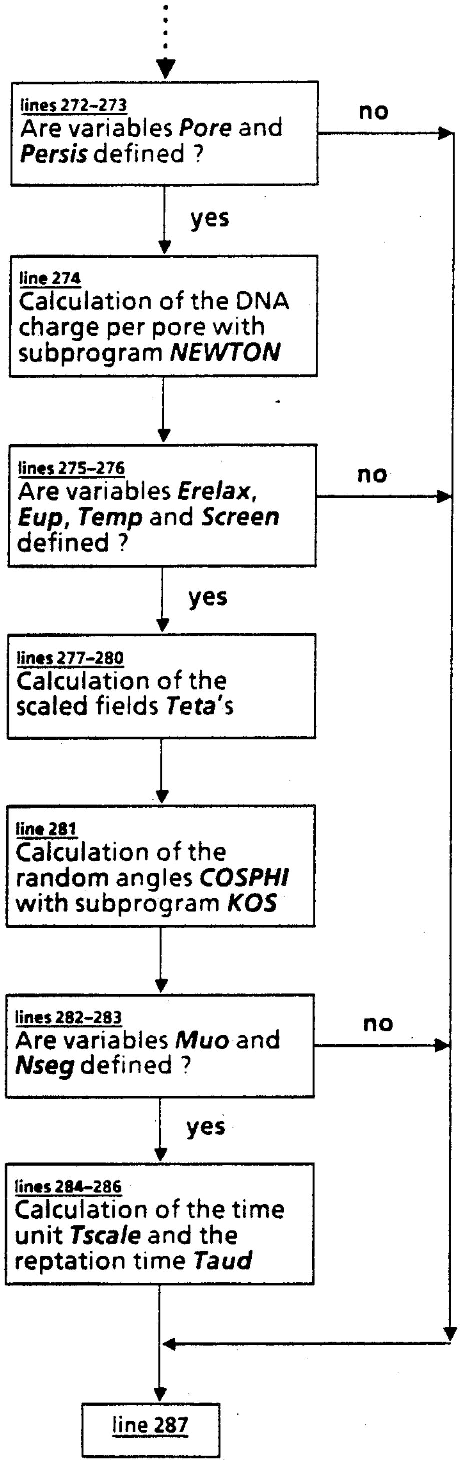
Figure 6C:
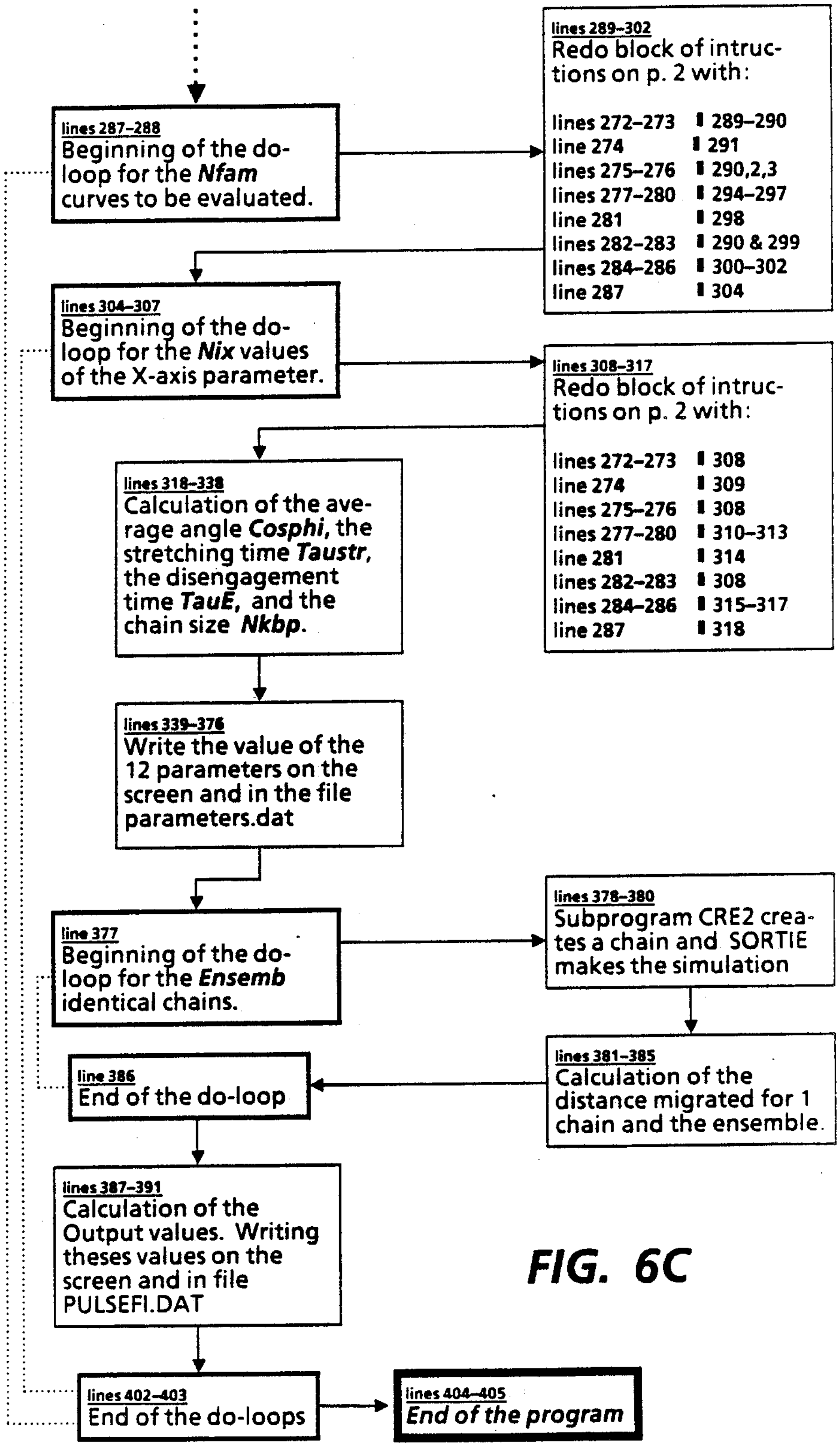
Figure 6D:
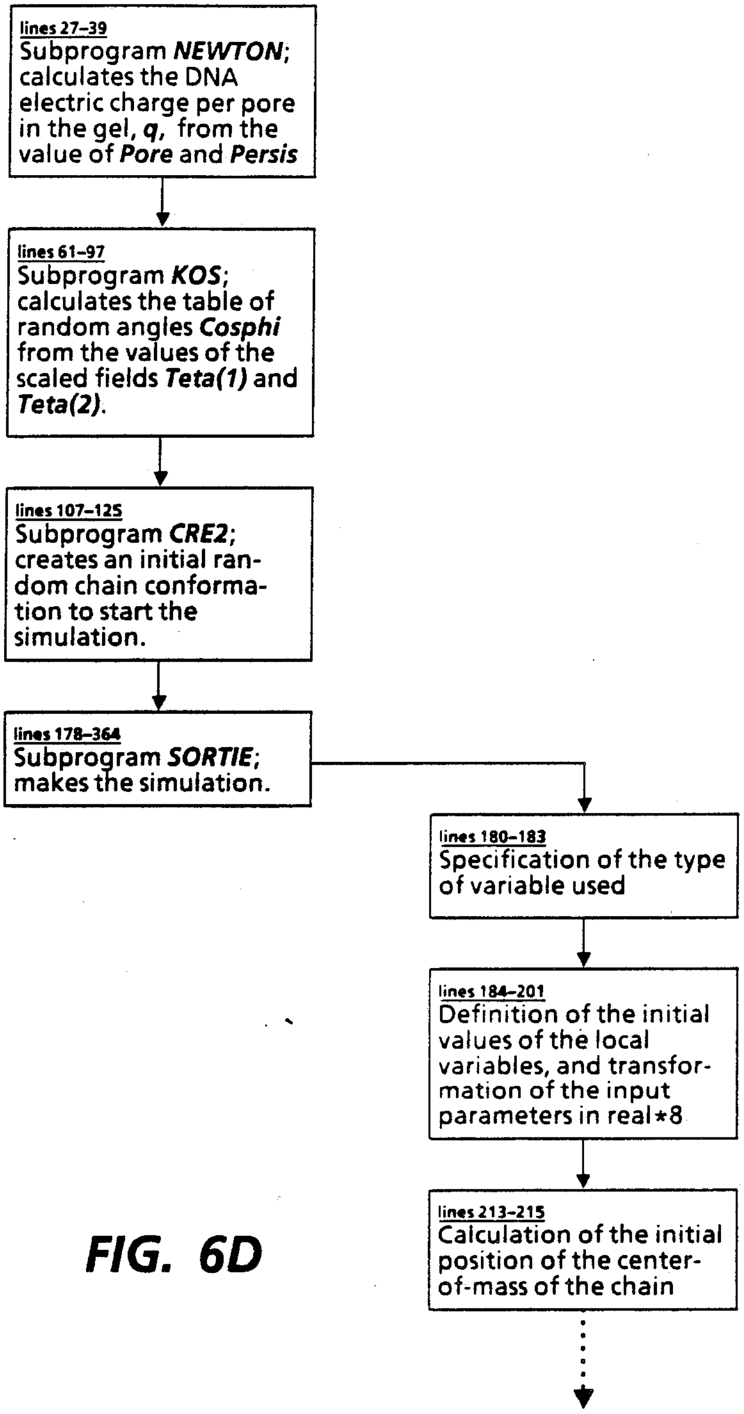
Figure 6E:
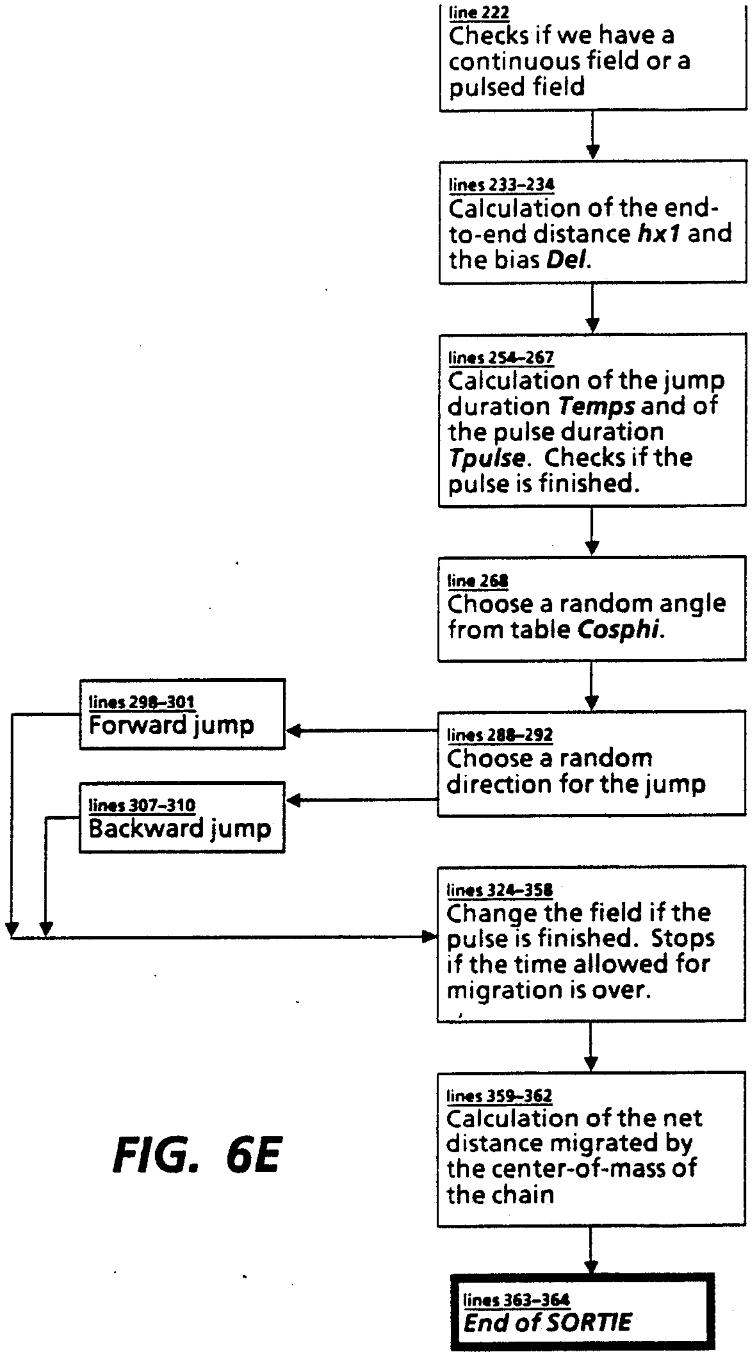

In one embodiment of the present invention the process comprises: (1) providing an electrophoresis device; (2) adding to the device a solution mixture containing DNA fragments of different lengths; (3) energizing the device, thereby creating a sequence of unidirectional uniform electric field pulses therein, said sequence of field pulses alternating between primary positive voltage pulses, and secondary pulses of a negative or positive polarity and of lesser voltage than the primary pulses; (4) calculating the time duration and the field strength required for the primary and secondary field pulses to enable resolution of the fragments into separate and distinct groups corresponding to the lengths of the DNA fragments present in each band; and (5) applying the selected primary and secondary fields with intensities and durations corresponding to the size of fragments to be separated, as calculated in step (4).

The electrophoresis device that may be selected for practicing the invention includes a standard gel electrophoresis cell of the type commonly available commercially, such as the Model H1 available from Bethesda Research Laboratories Life Technologies Inc. (P.O. Box 6009, Gaithersburg, Md. 20877) or the Model H3 available from the same company. The device generally contains an anode, a cathode, and a gel bed. Also, the dimensions of the Model H1 are 47×22×12.5 centimeters; the gel bed is 25×20 centimeters; the distance between the electrodes is 41 centimeters; and the platinum electrodes (0.25 millimeter diameter) are 19 centimeters across the gel bed. The box is constructed of plexiglass and contains 2.5 liters of buffer solution. The dimensions of the Model H3 are 37×12.8×6.5 centimeters; the gel bed is 14×11 centimeters; the distance between the electrodes is 31 centimeters; and the platinum electrodes (0.25 millimeter diameter) are 9.5 centimeters across the gel bed. The gel bed is constructed of plexiglass and contains 0.9 liter of buffer solution. Two electrodes are sufficient, and they may be of any noncorrosive metal, although platinum wire is preferred.

A solution mixture containing DNA fragments is placed in the gel bed of the device. One solution generally contains a gel comprising a weak agarose solution containing at least 0.2 percent by weight of agarose dissolved in a buffer at high temperature (about 60° C.).

The concentration of agarose should be at least 0.2 percent, and no more than 2 percent, with the preferred values being between 0.3 and 1 percent. A preferred gel is Agarose NA, a high purity grade gel available from Pharmacia AB, Molecular Biology Division, Uppsala, Sweden, lot numbers T02661 (electroendosomosis specification is −0.12), and T09920 (electroendosomosis specification is −0.13), for which the gel strength at 1.5 percent is in the range between 2,200 and 2,400 $gm/cm^2$ (grams per centimeter squared) are acceptable. Pore size of the gel may have a range of 30 to 300 nanometers with the preferred size being in the range of 60 to 200 nanometers. The gel may have a thickness of 0.2 to 2 centimeters with the preferred value being around 0.5 centimeter. The buffer comprises a solution of 0.089M tris base (Trizma base, Sigma Chemical Co., St. Louis, Mo.), 0.089M boric acid, and 0.002M EDTA (ethylenedinitrolo tetraacetic acid disodium salt).

The DNA fragments may be obtained from any source. Examples of DNA fragments that have been successfully separated using the process of the present invention include horse, yeast, human, and bacteria phage lambda. Three different DNA yeast strains utilized in the process of the present invention (A364, DC04α, YP80α) were obtained from Dr. David Thomas, Institut de Recherches en Biotechnologie, a/s Hôpital Royal Victoria, Pavillon Hersey, 687 Ave. des Pins Ouest, Montréal, Québec, Canada H3A 1A1. Human DNA from various sources was also used as obtained, for example, from the Human Genetics Mutant Repository, National Institute of General Medical Sciences, Camden, N.J. 08103. The small fragments which were obtained from Bethesda Research Laboratories Life Technologies, Inc. consist of λ-DNA/-HIND-III fragments ranging from 2.0 to 23.1 kilobases (cat. #5612SA), and of High MW DNA markers ranging from 8.3 to 48.5 kilobases (cat. #5618SA).

DNA multimer mixtures may be prepared by procedures based on the technique described by Van der Bleik et al. in *Molecular and Cellular Biology*, Vol. 6, No. 5, page 1671 (1986), the disclosure of which is totally incorporated herein by reference. The small fragments may be loaded into the gel using a 50 percent solution of fragments and 50 percent solution of 1 percent agarose (LMP agarose, ultrapure, cat. #5517UB, from Pharmacia AB, Molecular Biology Division, Uppsala, Sweden provides good results). This solution is placed in a syringe and delivered into the gel block. For human DNA, the preferred method of preparing the DNA and transferring it into the gel is a modified version of the technique described by K. Gardiner, W. Laas, and D. Patterson in *Somatic Cell and Molecular Genetics*, Vol. 12, No. 2, pages 185–195 (1986), the disclosure of which is totally incorporated herein by reference. For the DNA multimers, the preferred method of preparing the DNA and transferring it into the gel is a modified version of the technique described by Van der Bleik et al. in *Molecular and Cellular Biology*, Vol. 6, No. 5, page 1671 (1986). Finally, for yeast DNA, the preferred method of preparing the DNA and transferring it into the gel is a modified version of the technique described by C. R. Cantor and D. C. Schwartz in *Cell*, Vol 37, pages 67–75 (1984).

The electric field that energizes the gel electrophoresis device is generated by a custom-made power supply. The timed power supply for low-voltage electrophoresis work is designed as a self-contained direct current power supply capable of supplying 100 milliamps current at voltages between 0 and ±100 volts. Built into the power supply are two timers to control the intervals of time for which current will be switched on, off, or reversed. These timers are counters that alternately count pulses supplied by a crystal oscillator, which oscillator is a switch programmable device that is set to issue 10 pulses per second. While it is possible to set the unit to provide minimum on and off (or reverse) times of 1/10 seconds, in practice the timers cycle erratically due to circuit time constants, and the lower limit of on to off (or reverse) periods should be about 1 second. Electronic keyboard present counters are used to input the values for the pulse durations. The electronic keyboard preset counters Model No. GO 711.100 were obtained from Hecon Canada, Inc., 421 Carlingview Drive, Rexdale, Ontario, Canada M9W 5G7. The programmable crystal oscillators PXO series were obtained from Electro Sonic, Inc., 1100 Gordon Baker Road, Willowdale, Ontario, Canada M2H 3B3.

The duration of the applied field pulses is chosen according to the size of the largest fragment to be separated in the DNA mixture. Other factors to be considered are the buffer component and concentration, temperature, pore size (or agarose concentration), field strength, and net charge per unit length of the DNA fragments. The primary field may be applied for pulses of about ten seconds to about one thousand seconds, while the secondary field may be applied for pulses of from about ten seconds to about three thousand seconds.

Figure 7A:
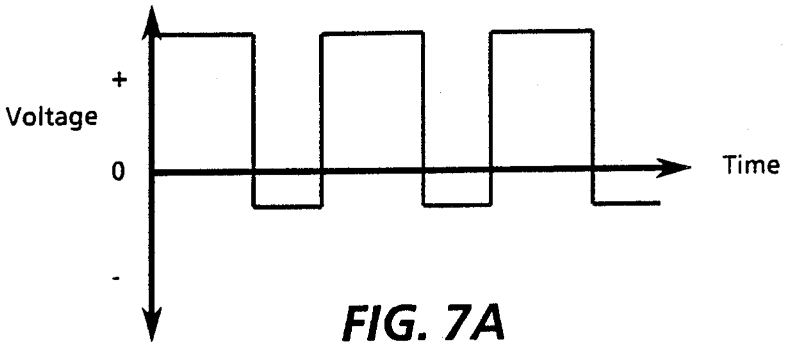
FIGS. 7A, 7B, 7C, 7D, and 7E are plots of voltage versus time which depict examples of field pulse shapes suitable for the process of the present invention.
Figure 7B:
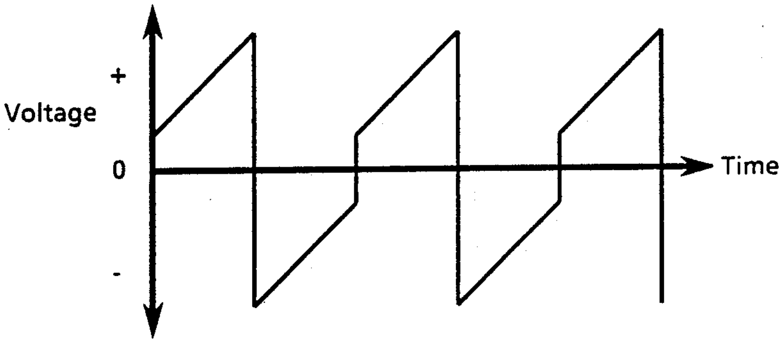

The electric field pulses are not limited to any particular shape. By shape is meant the rapidity or graduality with which the voltage increases with respect to time when a pulse is applied. A plot of voltage versus time illustrates the concept of field shape. For example, a square field pulse is one wherein the voltage increases immediately to the value determined to be optimal, and remains at that value for the entire duration of the pulse. A voltage versus time plot for such a field is depicted in FIG. 7A. The voltage versus time plot depicted in FIG. 7A is a plot of a square field pulse. The voltage may range between about +2.5 and about −2.5 volt/cm. Time may range between about 10 and about 1,000 seconds for primary pulses and between about 10 and about 3,000 seconds for secondary pulses. Other potentially useful field shapes include a triangular increasing field, as depicted in FIG. 7B. The voltage versus time plot depicted in FIG. 7B is a plot of a triangular increasing field pulse. The voltage may range between about +2.5 and about −2.5 volt/cm. Time may range between about 10 and about 1,000 seconds for primary pulses and between about 10 and about 3,000 seconds for secondary pulses.

Figure 7C:
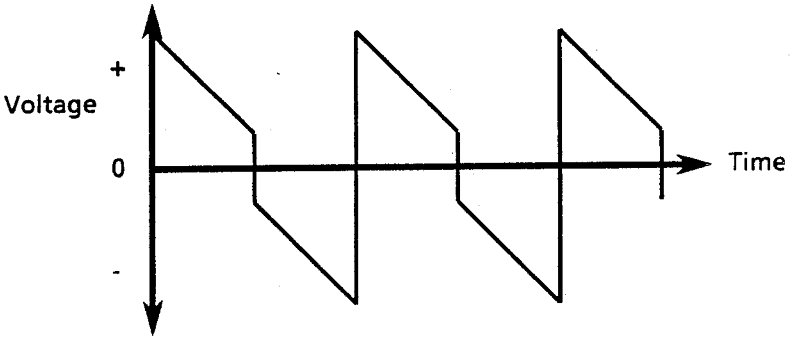

Another potentially useful field shape is a triangular decreasing field, as depicted in FIG. 7C. The voltage versus time plot depicted in FIG. 7C is a plot of a triangular decreasing field pulse. The voltage may range between about +2.5 and about −2.5 volt/cm. Time may range between about 10 and about 1,000 seconds for primary pulses and between about 10 and about 3,000 seconds for secondary pulses.

Figure 7D:
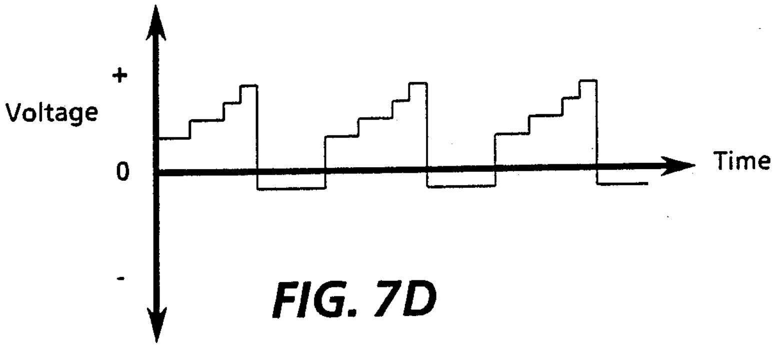

Yet another potentially useful field shape is a stepwise increasing field, as depicted in FIG. 7D. The voltage versus time plot depicted in FIG. 7D is a plot of a stepwise increasing field pulse. The voltage may range between about +2.5 and about −2.5 volt/cm. Time may range between about 10 and about 1,000 seconds for primary pulses and between about 10 and about 3,000 seconds for secondary pulses.

Figure 7E:
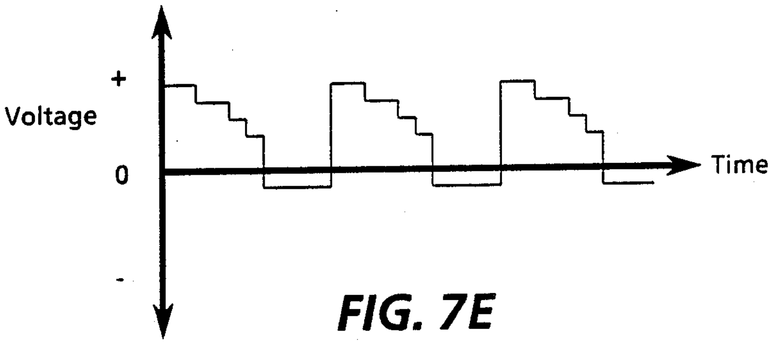

Still another potentially useful field shape is a stepwise decreasing field, as depicted in FIG. 7E. The voltage versus time plot depicted in FIG. 7E is a plot of a stepwise decreasing field pulse. The voltage may range between about +2.5 and about −2.5 volt/cm. Time may range between about 10 and about 1,000 seconds for primary pulses and between about 10 and about 3,000 seconds for secondary pulses. The field shape is not limited to those described; many other shapes are possible. The shape of the field may be chosen for each separation to be performed in order to optimize separation of the fragments. A field of a particular shape may better match the microscopic stretching and relaxation processes responsible for a particular DNA separation than would other field shapes.

Fragment separation is determined in terms of how far each group of fragments of a given size has travelled during the period in which the electric field was applied. Dye markers of ethidium are used to stain the entire gel. The gel is then illuminated with ultra-violet light, and the images are recorded by an ultraviolet sensitive camera (UV transilluminator), using a 550 nanometers long-pass filter, such as the one that may be obtained from Ultraviolet Products Inc., San Gabriel, CA. Alternatively, a Joyce-Lobel densitometer Chromoscan 3 model can be used to trace the bands in the gel. Use of a computer program simulating a pulsed field gel electrophoresis experiment, such as the one outlined in FIG. VI and included in Appendix I, can also be used to analyze the results.

A computer program for facilitating a DNA gel electrophoresis process may provide a preferred method of practicing the present invention in some instances. Such a program allows for continuous recalculation of the optimal experimental parameters as the experiment progresses, taking into account alterations in conditions that occur during the course of the process. In addition, such a program provides a rapid means of performing the calculations required for practicing the present invention, and also provides another means of identifying the groups of fragments separated at the end of the experiment. A program has been created that allows the user to vary the following parameters:

1—The fragment size
2—The density of agarose in the gel
3—The persistence length of DNA
4—The temperature
5—The viscosity of the buffer
6—The screening factor due to the ionic strength of the buffer
7—The time duration of the different pulses (primary and secondary)
8—The value and the direction of the electric field during the different pulses (primary and secondary).

When values for these parameters have been provided, the program provides the following results:

1—The velocity of each fragment in centimeters/-day.
2—The position of each fragment, i.e. the position of each band, in the gel after an experiment of a given duration.
3—The width of each band after an experiment of a given duration.

The equations for the dynamics of the DNA molecule used in this program are provided by an extension of the equations set forth above.

A flow chart for the program described appears in FIG. 6. The source code for this particular program appears in Appendix I. This program constitutes a method for choosing the proper experimental conditions to separate large DNA fragments by pulsed field gel electrophoresis. By using the program for various values of the experimental parameters, one can identify conditions that would allow separation of the relevant fragments with the available apparatus. Given the experimental conditions and the results of the experiment, one can also use the program to calculate the size fo the fragments present in each band in the gel at the end of the experiment. In many cases, no standard is necessary to identify the bands according to the size of fragments contained in them.

The following working examples are illustrative in nature and are not intended to limit the scope of the invention in any way. Other equivalent methods of practicing the present invention may occur to those skilled in the art.

EXAMPLE I

Using a Single Field

DNA "multimer" fragments with lengths of 1 to approximately 20×42,000 base pairs were prepared by procedures based on the technique described by Van der Bleik et al. in *Molecular and Cellular Biology*, Vol 6, No. 5, page 1671 (1986), the disclosure of which is totally incorporated herein by reference. The fragments were formulated in a 0.4 percent agarose gel in a buffer comprising a solution of 0.089M tris base, 0.089M boric acid, and 0.002M EDTA, and added to a Model H1 electrophoresis device, available from Bethesda Research Laboratories Life Technologies, Inc. Easily separable High Molecular Weight (HMW) fragments with known sizes of 8,300 to 48,500 base pairs, and λ-DNA/-HIND-III fragments ranging from 2,000 to 23,100 base pairs were also added to the gel as standard markers to help identify by comparison the large DNA fragments separated.

Estimates of the values of $\tau_{str.}$, $\tau_E$ and $\tau_D$ calculated using the following microscopic parameters:

Screening factor = 50 percent (a typical value)

Average pore size for 0.4 percent agarose $\alpha = 200$ nanometers

Mobility of DNA in free solution $\mu_0 = 0.0002$ cm$^2$/v sec.

Persistence length of DNA p = 67 nanometers (All values are from N. C. Stellwagen, *Biopolymers*, Vol. 24, pages 2243–2255 (1985).)

From these parameters, it was calculated that $q \approx 1060e$, where $e = 1.6 \times 10^{-19}$ coulomb (the bare electric charge of a DNA base). This calculation is based on the use of the Kratky-Porod equation discussed by O. J. Lumpkin et al., in *Biopolymers*, Vol. 24, pages 1573–1593 (1985), the disclosure of which is totally incorportated herein by reference.

The times obtained using the equations appearing above are presented in FIG. 1 with the calculations being based on the assumptions that the electric field is +1.46 v/cm (60 volts between electrodes 41 centimeters apart), that zero-field conditions are applied between the pulses of positive voltage, and that the temperature is 22° C. The results of the calculations appearing in FIG. 1 lead one to predict that at least 2 to 3 multimer fragments (84 to 126 kilo base pairs) will be separated by this choice of times. The experimental parameters were then selected on the basis of these calculations.

An electric field of +1.46 volt/cm was applied across the gel box in square shaped pulses of 30 seconds, and zero-field conditions were applied for 90 seconds between pulses; and the electric current was 35 milliamps. The process was continued for a period of 75 hours at a temperature of approximately 22° C. The results of the process are presented in FIG. 2. As seen from this table, the first 6 multimers (up to 252 kilo base pairs) were separated. The resulting separation was traced by using ethidium dye markers to stain the gel. The gel was then illuminated with ultraviolet light and the locations of the fragment groups were recorded by an ultraviolet sensitive camera (UV transilluminator) using a 550 nanometers long-pass filter.

EXAMPLE II

Using a Reverse Field

The DNA "multimers" were prepared by repeating the procedures of in Example I in an agarose gel containing 0.6 percent by weight of agarose. Easily separable High Molecular Weight (HMW) fragments with known sizes of 8,300 to 48,500 base pairs and λ-DNA/-HIND-III fragments ranging from 2,000 to 23,100 base pairs were also added to the gel as standard markers to help identify by comparison the large DNA fragments separated in the process. Moreover, yeast samples (100 to over 1,000 kilo base pairs) obtained from Dr. David Thomas were also added to prove the usefulness of the technique for separating chromosomal DNA.

Estimates of the values of $\tau_{str.}$, $\tau_E$, and $\tau_D$ were calculated using the following microscopic parameters:

Screening factor=50 percent (a typical value)

Average pore size for 0.6 percent agarose $\alpha=142$ nanometers

Mobility of DNA in free solution $\mu_0$0.0002 $cm^2$/V.sec.

Persistence length of DNA p=67 nanometers (all values are from N. C. Stellwagen, *Biopolymers*, Vol. 24, pages 2243–2255 (1985).)

From these parameters, it was calculated that $q \approx 617e$, where $e=1.6\times10^{-19}$ coulomb (the bare electric charge of a DNA base); this calculation is based on the use of the Kratky-Porod equation.

The results of the calculations for electric fields of +2 volt/cm and −1 volt/cm and a temperature of 22° C., as presented in FIG. 3, lead one to predict that multimers of up to 300 kilo base pairs will easily be separated with 90 second, +2 volt/cm primary field pulses, alternating with 90 second, −1 volt/cm secondary field pulses, since 90 seconds is between $\tau_{str.}$ and $\tau_E$ for both field intensities for the 300 kilo base fragment.

An electric field of +2.0 volt/cm (82 volts between electrodes 41 centimeters apart) was applied in primary pulses of approximately 90 seconds. During the period between these pulses, a secondary field of −1.0 volt/cm (41 volts between electrodes 41 centimeters apart) was applied for pulses of approximately 90 seconds. The applied field, including both primary and secondary pulses, was square in shape. The other conditions were as described in Example I. The process was continuted for a total period of 115 hours. The starting positions of the different DNA samples in the gel, as well as the number of fragments well separated at the end of the electrophoresis process, are presented in FIGS. 4 and 5. As seen from these tables, the first 10 multimers were separated in this process; accordingly, this combination of parameters was able to separate all the fragments having less than 420 kilo base pairs. Moreover, other bands begin to form, and the yeast chromosomes are clearly separated into 8 bands.

Other modifications of the present invention may occur to those skilled in the art based upon a reading of the present disclosure; these modifications are intended to be included within the scope of the present invention.

APPENDIX I

```
cccccccccccccccccccccccccccccccccccccccccccccccccccccccccccccccc
c   The goal of PULSE3.FOR is to calculate the displacement, the mobi-
c   lity and the velocity of DNA fragments during pulse-field gel
c   electrophoresis.  This is realized by considering 12 parameters,
c   two being variable.
c
c   List of those 12 parameters:
c     p(1) =eup     = field applied during the first pulse, also called
c                     field-pulse.  (V/cm)
c     p(2) =erelax  = field applied during the second pulse, also called
c                     field-relaxation.  (V/cm)
c     p(3) =teup    = duration of the first pulse, also called
c                     pulse duration.  (sec)
c     p(4) =trelax  = duration of the second pulse, also called
c                     relaxation time.  (sec)
c     p(5) =nseg    = number of segments forming a DNA molecule.
c                     (segments)
c     p(6) =ensemb  = number of DNA molecules composing the ensemble.
c                     (chains)
c     p(7) =duree   = duration of an electrophoresis performed for a
c                     given ensemble in this simulation, also called
c                     duration of an experiment.  (hours)
c     p(8) =pore    = poresize of a uniform gel. (Angstroms)
c     p(9) =persis  = persistence length of DNA molecules.  (Angstroms)
c     p(10)=temp    = temperature of an experiment.  (oC)
c     p(11)=muo     = DNA mobility at zero agarose concentration
c                     (cm**2)/(V*sec)- (related to solvent friction)
c     p(12)=screen  = screening effect of the cations in solution that
c                     lowers the number of net charges available on
c                     a molecule.  This value is expressed as a % of
c                     the total available charge.
c
cccccccccccccccccccccccccccccccccccccccccccccccccccccccccccccccc
```

```
      integer h,i,ii,j,k,l,ix,nix,iy,seed,ifam,nfam
      real p(12),teup,trelax,eup,erelax,pore,taue,taud,taustr,
     +duree,xmin,xmax,q,hxm(4,100,20),test1,test2,dx,muo,screen,dtl,
     +nkbp,unsurt,teta(2),x(100),fam(20),distan,nseg,ensemb,pi,qq,
     +tscale,avecos,temp,betaqa,cothte
      real trans(12)/100.0,100.0,1.0,1.0,1.0,1.0,3600.0,1.0e-10,
     +1.0e-10,1.0,0.0001,1.0/
      real*8 chain(10001),sum1,sum2,cosphi(2,0:4999)

      equivalence (p(1),eup),(p(2),erelax),(p(3),teup),(p(4),trelax),
     +(p(5),nseg),(p(6),ensemb),(p(7),duree),(p(8),pore),
     +(p(9),persis),(p(10),temp),(p(11),muo),(p(12),screen)

      character*21 para(12)/'field-pulse','field-relaxation',
     +'pulse duration','relaxation time','# seg. (int.GE.1)',
     +'ens. size (int.GE.2)','duration of exp.','poresize',
     +'persistence length','temperature','mobility 0',
     +'screen (0.0-1.0)'/

      character*12 units(12)/' V/cm',' V/cm',' sec',' sec',
     +' segments',' chains',' hours',' Angstroms',
     +' Angstroms',' oC',' cm**2/V*sec',' '/

      character*18 axey(4)/'Distance','Width of band','Velocity',
     +'Velocity variance'/

      character*6 unity(4)/'cm','cm','cm/day','cm/day'/

cccccccccccccccccccccccccccccccccccccccccccccccccccccccccccccccc
c     Determination of the x axis or the first variable.
cccccccccccccccccccccccccccccccccccccccccccccccccccccccccccccccc

      write(6,*)'Select a number for the parameter of the X axis.'
      do 10 i=1,12
10    write(6,*)i,'=',para(i)
      read(5,*) ix
15    write(6,*)'Minimum on X axis for ',para(ix),'; units=',units(ix)
      read(5,*)xmin
      xmin=xmin*trans(ix)
      if (ix.eq.5.or.ix.eq.6) then
      test1=jint(xmin)-xmin
      test2=abs(xmin)-xmin
         if(test1.ne.0.0.or.test2.ne.0.0)then
         write(6,*)'You must enter a positive integer value.'
         goto 15
         endif
         if(ix.eq.6.and.xmin.lt.2)then
         write(6,*)'You must enter an integer value greater than one.'
         goto 15
         endif
      endif
      if(ix.eq.12)then
         if(xmin.gt.1.0.or.xmin.lt.0.0)then
         write(6,*)'You must enter a real value between 0.0 and 1.0.'
         goto15
         endif
      endif
20    write(6,*)'Maximum on X axis for ',para(ix),'; units=',units(ix)
      read(5,*)xmax
      xmax=xmax*trans(ix)
      if (ix.eq.5.or.ix.eq.6) then
      test1=jint(xmax)-xmax
      test2=abs(xmax)-xmax
         if(test1.ne.0.0.or.test2.ne.0.0)then
         write(6,*)'You must enter a positive integer value.'
         goto 20
         endif
      endif
      if(ix.eq.12)then
         if(xmax.gt.1.0.or.xmax.lt.0.0)then
         write(6,*)'You must enter a real value between 0.0 and 1.0.'
         goto20
         endif
      endif
21    write(6,*)'What is the number of parameters between extrema?'
      read(5,*)nix

cccccccccccccccccccccccccccccccccccccccccccccccccccccccccccccccc
c   Calculation of the value of each interval on the X axis.
cccccccccccccccccccccccccccccccccccccccccccccccccccccccccccccccc
```

```
      if(nix.ne.1)then
      dx=(xmax-xmin)/(nix-1.0)
      else
      dx=1.0
      endif
      do 25 i=1,nix
      x(i)=xmin+(i-1.0)*dx
      if(ix.eq.5.or.ix.eq.6)then
         test1=jint(x(i))-x(i)
         if(test1.ne.0.0)then
           write(6,*)'You must choose a value for the number of'
           write(6,*)'parameters between extrema that gives integers.'
           goto21
         endif
      endif
25    continue

      write(6,*)'Enter a seed. (high value of an integer*4 and odd)'
      read(5,*)seed

cccccccccccccccccccccccccccccccccccccccccccccccccccccccccccccccccccccc
c   Definition of curve family, that is the second variable.
cccccccccccccccccccccccccccccccccccccccccccccccccccccccccccccccccccccc

      write(6,*)'Select a number for the parameter that defines the'
      write(6,*)'family of curves.'
      do 30 i=1,12
         if (i.eq.ix) goto 30
      write(6,*)i,'=',para(i)
30    continue
      read(5,*)ifam
26    write(6,*)'How many curves of the ',para(ifam)
      write(6,*)'family do you want? (maximum=20)'
      read(5,*)nfam
         if(nfam.gt.20)then
         write(6,*)'You must choose an integer smaller than 21.'
         goto 26
         endif
      do 35 i=1,nfam
36    write(6,*)'What is the value of ',para(ifam)
      write(6,*)'units =',units(ifam),'for the curve no.',i
      read(5,*)fam(i)
      fam(i)=fam(i)*trans(ifam)
      if (ifam.eq.5.or.ifam.eq.6) then
      test1=jint(fam(i))-fam(i)
      test2=abs(fam(i))-fam(i)
         if(test1.ne.0.0.or.test2.ne.0.0)then
         write(6,*)'You must enter a positive integer value.'
         goto 36
         endif
      endif
      if(ifam.eq.6.and.fam(i).lt.2)then
         write(6,*)'You must enter an integer value greater than one.'
         goto 36
      endif
      if(ifam.eq.12)then
         if(fam(i).gt.1.0.or.fam(i).lt.0.0)then
         write(6,*)'You must enter a real value between 0.0 and 1.0.'
         goto 36
         endif
      endif
35    continue

cccccccccccccccccccccccccccccccccccccccccccccccccccccccccccccccccccccc
c   Definition of all other parameters
cccccccccccccccccccccccccccccccccccccccccccccccccccccccccccccccccccccc

      do 40 i=1,12
         if(i.eq.ix.or.i.eq.ifam)goto 40
45    write(6,*)'What is the value of ',para(i),'units =',units(i)
      read(5,*)p(i)
      p(i)=p(i)*trans(i)
         if (i.eq.5.or.i.eq.6) then
         test1=jint(p(i))-p(i)
         test2=abs(p(i))-p(i)
            if(test1.ne.0.0.or.test2.ne.0.0)then
            write(6,*)'You must enter a positive integer value.'
            goto 45
            endif
         endif
```

```
        if(i.eq.11)then
          if(p(i).gt.1.0.or.p(i).lt.0.0)then
        write(6,*)'You must enter a real value between 0.0 and 1.0.'
          goto45
          endif
        endif
40    continue

cccccccccccccccccccccccccccccccccccccccccccccccccccccccccccccccccccccc
C   unsurt= electric charge/(2*Kb)=(1.602189e-19 Coulomb)/(2 *
C   1.380662e-23 J/K)
cccccccccccccccccccccccccccccccccccccccccccccccccccccccccccccccccccccc

      unsurt=5.80226e3
      pi=acos(-1.0)

cccccccccccccccccccccccccccccccccccccccccccccccccccccccccccccccccccccc
C   The subroutine NEWTON determines the value of q, the total
C   charge on each DNA segment.  The subroutine KOS creates the
C   table for the values of cosphi (the angles an end-segment can
C   make with the field direction). The subroutine CRE2 creates the
C   initial chain and SORTIE computes the displacement of this chain.
C   The loop 100 is for curves family.  The loop 110 serves for the
C   variable X parameter and is used for the final calculation of the
C   outputs.  The loop 120 is for the calculation of the different
C   outputs of each chain created.
C
C   tscale is the time taken for each jump by the end-segment of a
C   given chain.  tscale is derived from the definition of the curvi-
C   linear diffusion coefficient (Dc) and the curvilinear viscosity
C   coefficient (zetac) which is:
C       Dc=Kb x T/zetac  where zetac=N x zetal and Dc=a**2/(2 x delt t)
C       delt t = tscale
C       tscale=a**2/(2 x Dc) =N x zetal x a**2/(2 x Kb x T)
C             =N x dtl
C
C   dtl represents the time it takes for a one-segment chain to
C   jump.  This time is defined partly by the viscosity coefficient
C   of one segment (zetal).
C       dtl=zetal x a**2/(2 x Kb x T)  where zetal=Q/(3 x N x muo)
C       dtl=Q x a**2/(6 x N x muo x Kb x T) where Q=q/N
C          =q x a**2/(6 x muo x Kb x T)
C          =q x a**2 x unsurt/(3 x muo)
C
C   taustr is the characteristic time of chain stretching for small
C   times.  The definition is given in Slater, G.W.; Noolandi, J;
C   "Prediction of Chain Elongation in the Reptation Theory of DNA Gel
C   Electrophoresis"; Biopolymers, Vol. 24, No. 12, December 1985, pp.
C   2181-2184.  It's the equation (5).
C       taustr=tscale/(teta(1) x <cosphi>)
C   where <cosphi> is calculated from table cosphi
C
C
C   taud, the reptation time, is defined in DeGennes' paper (1971).
C       taud=2 x N**2 x tscale/pi**2
C
C   taue is the drift disengagement time.
C
C
C       taue=(N x tscale x a)/(teta x <hx>)
C              where <hx>=sqrt{(2 x N)/(3 x pi)} x a
C       taue=(N x tscale)/(teta x sqrt{(2 x N)/(3 x pi)})
C       taue=(N**0.5 x tscale)/(teta x sqrt{(2/(3 x pi)})
cccccccccccccccccccccccccccccccccccccccccccccccccccccccccccccccccccccc

      open(11,file='PULSEFI.DAT',status='new',access='sequential')
      open(12,file='DISTAN.DAT',status='new',access='sequential')
      open(13,file='PARAMETERS.DAT',status='new',access='sequential')

cccccccccccccccccccccccccccccccccccccccccccccccccccccccccccccccccccccc
C   The two following conditions (nix.eq.1) and (nfam.eq.1) are set to
C   allow the calculation of all the variables if the two variable
C   parameters, ix and ifam, are constant during the simulation.
C   In this way, we avoid useless computation inside loops.
cccccccccccccccccccccccccccccccccccccccccccccccccccccccccccccccccccccc

      if(ix.eq.8.or.ix.eq.9)goto50
      if(ifam.eq.8.or.ifam.eq.9)goto50
         call NEWTON(pore,persis,q)
      if(ifam.lt.3.or.ifam.eq.10.or.ifam.eq.12)goto50
      if(ix.lt.3.or.ix.eq.10.or.ix.eq.12)goto50
```

```
              qq=q*screen
              betaqa=qq*pore*unsurt/(temp+273.13)
              teta(1)=betaqa*Eup
              teta(2)=betaqa*Erelax
              call KOS(teta,cosphi)
           if(ix.eq.11.or.ix.eq.5)goto50
           if(ifam.eq.5.or.ifam.eq.11)goto50
              dtl=pore*betaqa/(3.0*muo)
              tscale=dtl*nseg
              taud=2.0*nseg**2*tscale/pi**2
 50        do 100 i=1,nfam
          p(ifam)=fam(i)
           if(ix.eq.8.or.ix.eq.9)goto60
           goto(52,52,60,60,52,60,60,51,51,52,52,52)ifam
 51           call NEWTON(pore,persis,q)
 52        if(ix.eq.1.or.ix.eq.2.or.ix.eq.10.or.ix.eq.12)goto60
            if(ifam.eq.11.or.ifam.eq.5)goto53
             qq=q*screen
             betaqa=qq*pore*unsurt/(temp+273.13)
             teta(1)=betaqa*Eup
             teta(2)=betaqa*Erelax
             call KOS(teta,cosphi)
 53        if(ix.eq.5.or.ix.eq.10.or.ix.eq.11.or.ix.eq.12)goto60
              dtl=pore*betaqa/(3.0*muo)
              tscale=dtl*nseg
              taud=2.0*nseg**2*tscale/pi**2

 60      do 110 j=1,nix
              sum1=0.0d00
              sum2=0.0d00
              p(ix)=x(j)
              goto(62,62,70,70,63,70,70,61,61,62,63,62)ix
 61           call NEWTON(pore,persis,q)
 62           qq=q*screen
              betaqa=qq*pore*unsurt/(temp+273.13)
              teta(1)=betaqa*Eup
              teta(2)=betaqa*Erelax
              call KOS(teta,cosphi)
 63           dtl=pore*betaqa/(3.0*muo)
              tscale=dtl*nseg
              taud=2.0*nseg**2*tscale/pi**2
 70           avecos=0.0

ccccccccccccccccccccccccccccccccccccccccccccccccccccccccccccccccccccccccc
c
c   The calculation of taustr is performed by calculating the
c   average value of the numbers found in table cosphi.
c
c
ccccccccccccccccccccccccccccccccccccccccccccccccccccccccccccccccccccccccc

                  do 1000 ii=1,5000
 1000             avecos=avecos+sngl(cosphi(1,ii))
              avecos=avecos/5000.0
              cothte=1/tanh(teta(1))-1.0/teta(1)
              taustr=tscale/(teta(1)*avecos)
              if(teta(1).ne.0.0)then
                 taue=sqrt(nseg)*tscale/(teta(1)*sqrt(0.66666666/pi))
                 else
                 taue=0
              endif
              nkbp=q*nseg/2000.0
                 write(6,*)para(ifam),fam(i)/trans(ifam),units(ifam)
                 write(13,220)('Curves family')
 220             format(a16)
                 write(13,230)(para(ifam),fam(i)/trans(ifam),units(ifam))
 230             format(x,a21,e13.4,x,a11)
                 write(6,*)para(ix),x(j)/trans(ix),units(ix)
                 write(13,240)('X parameter(s)')
 240             format(a17)
                 write(13,230)(para(ix),x(j)/trans(ix),units(ix))
                 write(13,260)('All other parameters')
 260             format(a23)
                 do 150 ii=1,12
                 if(ii.eq.ix.or.ii.eq.ifam)goto150
                 write(6,*)para(ii),p(ii)/trans(ii),units(ii)
                 write(13,270)(para(ii),p(ii)/trans(ii),units(ii))
 270             format(x,a21,e14.7,x,a12)
 150             continue
            write(6,*)'avecos=',avecos,' coth teta(1)=',cothte
```

```
      write(6,*)'teta(1)',teta(1),' teta(2)',teta(2)
      write(6,*)'q',q,' nKbp',nkbp
      write(6,*)'dtl',dtl,' tscale',tscale
      write(6,*)'tau stretch            :',taustr
      write(6,*)'drift disengagement time:',taue
      write(6,*)'reptation time          :',taud
      write(6,*)' '
            write(13,279)('Parameters calculated in the program')
 279        format(a40)
            write(13,280)('teta(1): ',teta(1),'teta(2): ',teta(2))
 280        format(x,a9,e14.7,x,a9,e14.7)
            write(13,281)('  q: ',q,'charges  ','nKbp: ',nkbp,'Kbp')
 281        format(x,a5,e14.7,x,a10,a5,e14.7,x,a2)
         write(13,282)('dtl: ',dtl,' sec.;',' tscale: ',tscale,'sec.')
 282        format(x,a5,e14.7,x,a6,a9,e14.7,x,a4)
            write(13,283)('tau stretch             :',taustr,'sec.')
 283        format(x,a30,e14.7,x,a4)
            write(13,283)('drift disengagement time:',taue,'sec.')
            write(13,283)('reptation time          :',taud,'sec.')
            write(13,260)('-----------------------------')
            do 120 k=1,ensemb
            call CRE2(jint(nseg),seed,chain)
            call SORTIE(cosphi,seed,teup/tscale,trelax/tscale,
     +                duree/tscale,nseg,chain,teta,distan)
            distan=distan*pore*100.0
            sum1=sum1+distan
            sum2=sum2+distan**2
            write(12,210)(fam(i)/trans(ifam),x(j)/trans(ix),distan)
 210        format(3(e14.7,x))
 120        continue
            hxm(1,j,i)=sngl(sum1)/ensemb
            hxm(2,j,i)=sqrt(abs(sngl(sum2)-sngl(sum1**2)/
     +               ensemb)/(ensemb-1))
            hxm(3,j,i)=hxm(1,j,i)*86400.0/duree
            hxm(4,j,i)=hxm(2,j,i)*86400.0/duree
            write(6,*)x(j)/trans(ix),units(ix),
     +                fam(i)/trans(ifam),units(ifam)
            write(6,*)axey(1),'= ',hxm(1,j,i),unity(1)
            write(6,*)axey(2),'= ',hxm(2,j,i),unity(2)
            write(6,*)axey(3),'= ',hxm(3,j,i),unity(3)
            write(6,*)axey(4),'= ',hxm(4,j,i),unity(4)
            write(6,*)' '
            write(11,200)(nkbp,x(j)/trans(ix),
     +                fam(i)/trans(ifam),((hxm(k,j,i)),k=1,4))
 200        format(e10.4,x,6(e14.7,x))
 110     continue
 100  continue
      stop
      end
```

```
cccccccccccccccccccccc   SUBROUTINE NEWTON   ccccccccccccccccccccccc
ccccccccccccccccccccccccccccccccccccccccccccccccccccccccccccccccccc
c   The subroutine NEWTON is used to calculate the total charge q
c   of a DNA segment.  The pore diameter a and the persistence
c   length p are used to calculate the total segment charge q.
c
c   The total charge is proportional to the chain contour-
c   length, l (there's two charges for each base-pair, 3.4 Angstrom).
c   To obtain l, the Kratky-Porod formula is used and is taken from
c   Lumpkin, Dejardin, Zimm (1985), Biopolymers, vol. 24, pp. 1573-
c   1593, (equation 20). In this subroutine the variable q is used for
c   l and at the end the value of q = q * 2/3.4e-10, q = q/1.7e-10
c
c   The roots of this equation are obtained by using the Newton-
c   Raphson method.  This method works for "well-behaved function" and
c   consists to start with any value of X that is near a root.  The
c   correspondind value of Y can be determine by the equation.  This
c   will represent a point on the curve which is not usually a root.
c   A tangent f(x1) is then constructed at this point on the curve and
c   extended until it intersects the X-axis.  The next approximation,
c   x2, is at this intersection on the X-axis.  This process is repea-
c   ted until the desired convergence is attained.  In this subroutine
c   the initial X value is 3000e-10meter and the relative convergence
c   criterion is 0.001.
ccccccccccccccccccccccccccccccccccccccccccccccccccccccccccccccccccc

      subroutine NEWTON(a,p,q)
      real p,a,y,dery,rapp,li,q

      q=3000.0e-10
```

```
10    y=q/p-1.0+exp(-q/p)-a**2/(2.0*p**2)
      dery=1.0/p-exp(-q/p)/p
      li=q
      q=li-y/dery
      rapp=abs((q-li)/(q+li))
      if (rapp.gt.0.001)goto 10
      q=q/1.7e-10
      return
      end


ccccccccccccccccccccccccc   SUBROUTINE KOS   cccccccccccccccccccccccc
ccccccccccccccccccccccccccccccccccccccccccccccccccccccccccccccccccccc
C   The subroutine KOS calculates the possible orientations
C   of a charged head-segment as a function of the applied electric
C   fields.  These values are used in SORTIE.
C   Double precision is necessary for the calculation because the log
C   of very small value is otherwise imprecise.  The equation used
C   here, cos(angle[0,180])=log(2*[0,1]*sinh(teta)+exp(-teta))/teta
C   where teta=q*E*a/(2*Kb*T), has been devised by Gary Slater.  It
C   takes into account the effect of the electric field on
C   the orientation of a charged head-segment leaving its
C   tube.
C
C   The size of the table is two rows of 5000 values.  One row corres-
C   ponding for each teta.  The first column begins at 0 instead of 1
C   simply to avoid one mathematical operation in the subroutine
C   SORTIE when comes the time to choose a value in this table.
ccccccccccccccccccccccccccccccccccccccccccccccccccccccccccccccccccccc

      subroutine KOS(teta,cosphi)
      integer i,j
      real teta(2)
      real*8 xsinh,zz,xexp,cosphi(2,0:4999)

      do 10 i=1,2

ccccccccccccccccccccccccccccccccccccccccccccccccccccccccccccccccccccc
C   In the case where teta=0, which means that the electric field=0,
C   the values of cosphi correspond to the probable distribution of
C   cos([0,180o]) in spherical coordinates.  It means an uniform
C   distribution between [-1,1].
ccccccccccccccccccccccccccccccccccccccccccccccccccccccccccccccccccccc

      if(teta(i).eq.0.0)then
         do 30 k=0,4999
30       cosphi(i,k)=(dflotj(k)-2499.5d00)/2499.5d00
         goto 10
      endif
      xsinh=2.0d00*dsinh(dble(teta(i)))
      xexp=dexp(dble(-teta(i)))
      do 20 j=0,4999

ccccccccccccccccccccccccccccccccccccccccccccccccccccccccccccccccccccc
C   The use of 5001 at the denominator instead of 5000 affords to get
C   rid of the data 0 and 1 in the interval [0,1] defined precedently
C   in the log expression.  We then have the interval ]0,1[.  This
C   bias is less important than the bias due to the presence of these
C   extrema data because their presence would give more weight than it
C   is really the case for the upper and lower values of the table.
ccccccccccccccccccccccccccccccccccccccccccccccccccccccccccccccccccccc

      zz=dflotj(5000-j)/5001.0d00
20    cosphi(i,j)=dlog(xsinh*zz+xexp)/dble(teta(i))
10    continue
      return
      end


cccccccccccccccccccccc   SUBROUTINE CRE2   ccccccccccccccccccccccccccc
ccccccccccccccccccccccccccccccccccccccccccccccccccccccccccccccccccccc
C   The subroutine CRE2 creates a three-dimensional chain by using a
C   random generator number.  Only the values for the X dimension are
C   calculated.
ccccccccccccccccccccccccccccccccccccccccccccccccccccccccccccccccccccc

      subroutine CRE2(n,seed,chain)
      integer n,numl,seed,i,zl
      real*8 chain(1001)

      chain(1)=0.0d00
      numl=n+1
```

```
cccccccccccccccccccccccccccccccccccccccccccccccccccccccccccccccccc
c   The term (dble(ran(seed))*2.0d00-1.0d00) in the loop represents
c   the different probable values of cos(angle[0,180o]) in spherical
c   coordinates.  That means a uniform distribution between [-1,1].
cccccccccccccccccccccccccccccccccccccccccccccccccccccccccccccccccc

      do 100 i=2,numl
      z1=i-1
      chain(i)=chain(z1)+(dble(ran(seed))*2.0d00-1.0d00)
100   continue
      return
      end


cccccccccccccccccccccc   SUBROUTINE SORTIE   cccccccccccccccccccccccc
cccccccccccccccccccccccccccccccccccccccccccccccccccccccccccccccccc
c   The subroutine SORTIE calculates the displacement of the chain in
c   its tube, considering the combined effect of the brownian motion
c   and the electrical drift.  Both ends can move but with different
c   probability.  The equations used in this subroutine are drawn
c   from: Slater, G.W.; Noolandi, J.;"On the Reptation Theory of Gel
c   Electrophoresis"; Biopolymers, vol.25, no.3, March 1986, pp 431-
c   453.
c
c   bead   = number of beads in the chain
c   cc     = it's the pointer that indicates the position of the
c            first bead of the chain
c   c5     = it's the pointer that indicates the position of the
c            last bead of the chain
c   chain  = vector which conserves the position of each beads.  When
c            the chain moves, the new value of position for the end-
c            segment that has made the jump is added to the vector and
c            the position of the last bead, which is the tail that
c            follows the rest of the body, disappeared. The vector
c            chain is used as if it was a circular vector
c   d(x)   = vector that is used as a minimal and maximal limit for the
c            number of beads or the number of values of the vector
c            chain.
c   del    = teta(x)*hxl, del is used to determine the probability of a
c            jump forward or backward.
c   distan= distance covered by the center of mass of the chain
c   duree  = total time duration of an experiment
c   hxl    = end-to-end distance of the chain
c   L      = a variable that can have the value 1 or 2, used to
c            indicate if the calculations are done for tup, 1, or for
c            trelax, 2.
c   nseg   = number of segments in the chain
c   pf     = final position of center of mass
c   po     = initial position of center of mass
c   pp(L) = vector that replaced tup and trelax in the subroutine so
c            they can be modified locally.
c   t      = total time taken for the sum of all tpulse
c   temps  = time taken for each jump
c   teta(x) = q*E*a/(2*Kb*T), teta(1) is for Eup and teta(2) is for
c            Erelax.
c   tpulse= sum of temps for a given tup or trelax
c   trelax= time taken when teta(2) is on (there's no field or teta(2)
c            is smaller than teta(1)
c   tup    = time taken when teta(1) is on (when the field is applied)
c   z      = is a variable having a value between [1,5000] which is de-
c            termined by using a random number.  Z will serve to choose
c            the value of cosphi.
cccccccccccccccccccccccccccccccccccccccccccccccccccccccccccccccccc

      subroutine SORTIE(cosphi,seed,tup,trelax,duree,nseg,chain,teta,
     +                  distan)
      integer seed,bead,d(0:10002),cc,seg,i,j,L,c5,z
      real teta(2),distan,tup,trelax,duree,nseg
      real*8 t,temps,del,po,pf,chain(10001),hxl,tpulse,cosphi(2,0:4999)
      real*8 pp(2),tate(2),dduree
      bead=nseg+1
      do 10 j=1,bead
10    d(j)=j
      d(0)=bead
      j=bead+1
      d(j)=1
      cc=1
      L=1
      tpulse=0.0d00
      t=0.0d00
```

```
      pp(1)=tup*1.0d00
      pp(2)=trelax*1.0d00
      tate(1)=1.0d00*teta(1)
      tate(2)=1.0d00*teta(2)
      dduree=1.0d00*duree
      pf=0.0d00
      po=0.0d00
      c5=bead

cccccccccccccccccccccccccccccccccccccccccccccccccccccccccccccccc
c   The calculation of the position of the center of mass is based on
c   the approximation that all the mass of a segment is concentrated
c   in the middle of this segment, the segment being linear.  That
c   means that the position of the center of mass Xcm
c       = sum of all Xi/n segments ,
c       ={(R1 + R2)/2 + (R2 + R3)/2 + ... (Rn + Rn+1)/2}/n segments
c          where Ri = the position of the ith bead
cccccccccccccccccccccccccccccccccccccccccccccccccccccccccccccccc

      do 15 i=1,bead
15    po=po+chain(i)
      po=(po-0.5d00*(chain(cc)+chain(c5)))/dble(nseg)

cccccccccccccccccccccccccccccccccccccccccccccccccccccccccccccccc
c   If tup is greater than duree, this is the conditions of a continu-
c   ous field. The value of tup is then set back to the value of duree.
cccccccccccccccccccccccccccccccccccccccccccccccccccccccccccccccc

      if(pp(1).gt.dduree)pp(1)=dduree

cccccccccccccccccccccccccccccccccccccccccccccccccccccccccccccccc
c   Initially, the end-to-end distance hxl is calculated here by sub-
c   stracting the position of the first bead to the last bead,
c   chain(bead)-chain(1). Thereafter, hxl corresponds to the differen-
c   ce between the new first bead and the new last bead.  This change
c   in the sign of hxl is used to avoid the negative sign in the
c   mathematical operation exp(-2.0*del).
cccccccccccccccccccccccccccccccccccccccccccccccccccccccccccccccc

20    hxl=chain(c5)-chain(cc)
      del=tate(L)*hxl

cccccccccccccccccccccccccccccccccccccccccccccccccccccccccccccccc
c   The time taken for each jump is quite different depending if the
c   chain is trapped in a dense conformation (a small end-to-end
c   distance) or if it is elongated (large value of hxl).  The time
c   function is expressed in the following way:
c   temps=tan.hyp.(del)/del where del is function of hxl.  When del=0,
c   a limiting condition is posed that set temps = to 1 because the
c   function temps has a singularity at this point.  This expression
c   has been derived by Gary Slater and is explained in a paper by
c   Slater G.; Rousseau, J; Noolandi, J; in press (Biopolymers,1987)
c
c   The calculation of temps and tpulse
c   is performed at the beginning of the loop.
c
c
c
cccccccccccccccccccccccccccccccccccccccccccccccccccccccccccccccc

      if(del.eq.0.0d00)then
         temps=1.0d00
         else
         temps=dtanh(del)/del
      endif
      tpulse=tpulse+temps

cccccccccccccccccccccccccccccccccccccccccccccccccccccccccccccccc
c   If the value of tpulse is greater than the value of tup or trelax
c   the calculations must be ended and there's an exit from the loop
c   beginning by 20.
cccccccccccccccccccccccccccccccccccccccccccccccccccccccccccccccc

      if(tpulse.gt.pp(L))goto50
      z=jint(ran(seed)*5000.0)

cccccccccccccccccccccccccccccccccccccccccccccccccccccccccccccccc
c   The direction of a jump by one of the end-head segment is given
c   by: probability= [0,1[ -1/(1+exp(-2*del)) which gives values
c   between ]-1,1[.  If the value of this number is negative or
c   equal to 0, the jump will be towards towards bead 1.
```

```
C   If the value is positive, the jumps
C   will be towards beads n.
C
C   This expression has been derived by Gary Slater
C   and is explained in a paper by Slater, G.; Rousseau, J.; Noolandi,
C   J; in press (Biopolymers, 1987).
C
C   To avoid the mathematical overflow of the mathematical function
C   exponential, that is the limit of the VAX as to the argument
C   allowed for the exponential, a condition is set to
C   verify the value of del before its use in an exponential.
cccccccccccccccccccccccccccccccccccccccccccccccccccccccccccccccccc

          if(dabs(del).le.40.0d00)then
             if(ran(seed)-1.0/(1.0+exp(2.0*sngl(del))))30,30,40
             else
             if(del)30,30,40
          endif

cccccccccccccccccccccccccccccccccccccccccccccccccccccccccccccccccc
C   -------------Towards bead 1, the end-head segment-----------------
cccccccccccccccccccccccccccccccccccccccccccccccccccccccccccccccccc

30        chain(c5)=chain(cc)+cosphi(L,z)
          cc=c5
          c5=d(c5-1)
          goto20

cccccccccccccccccccccccccccccccccccccccccccccccccccccccccccccccccc
C   ----------Towards bead n, the beginning-head segment--------------
cccccccccccccccccccccccccccccccccccccccccccccccccccccccccccccccccc

40        chain(cc)=chain(c5)+cosphi(L,z)
          c5=cc
          cc=d(cc+1)
          goto20

cccccccccccccccccccccccccccccccccccccccccccccccccccccccccccccccccc
C   Since a pulse is ended before the last jump took place, the exit
C   of the loop 20 necessitates the correction of tpulse in such a way
C   that tpulse corresponds to the effective displacement calculated
C   here.
C
C   The difference between tpulse and Tup or Tre introduces an error
C   whose cumulative effect on distan is considered negligeable. (This
C   error is due to the fact that the model used here considered
C   discrete time).
cccccccccccccccccccccccccccccccccccccccccccccccccccccccccccccccccc

50        tpulse=tpulse-temps
          t=t+tpulse

cccccccccccccccccccccccccccccccccccccccccccccccccccccccccccccccccc
C  The summation of tpulse given by t is tested to see if other calcu-
C  lations must be performed. If it's yes the variable L is reinitia-
C  lized so we can change from tup to trelax or vice-versa.  If it's
C  no, the final calculations are made and we go back to the main
C  program.
cccccccccccccccccccccccccccccccccccccccccccccccccccccccccccccccccc

          if(t.lt.dduree)then
             L=3-L
             tpulse=0.0d00

cccccccccccccccccccccccccccccccccccccccccccccccccccccccccccccccccc
C   The difference between the total time of the experiment, duree and
C   the total time, t, must be greater than 1 (1 is the time unit here
C   which is obtained when the subroutine SORTIE is called and all the
C   time parameters, teup, trelax and duree, divided by tscale).  This
C   condition permits to go out of the loop 20.
cccccccccccccccccccccccccccccccccccccccccccccccccccccccccccccccccc

             if((dduree-t).lt.1.0d00)goto55

cccccccccccccccccccccccccccccccccccccccccccccccccccccccccccccccccc
C  If the difference between the total time of the experiment, duree,
C  and the total time, t, taken till that moment is smaller than the
C  given time interval (tup or trelax), the remaining time interval is
C  set equal to that difference.
cccccccccccccccccccccccccccccccccccccccccccccccccccccccccccccccccc
```

```
            if((dduree-t).lt.pp(L))pp(L)=dduree-t
            goto20
         endif
55       do 60 j=1,bead
60       pf=pf+chain(j)
         pf=(pf-0.5d00*(chain(cc)+chain(c5)))/dble(nseg)
         distan=sngl(pf-po)
         return
         end
```

What is claimed is:

1. A process for enabling the separation of a mixture of DNA fragments comprising: (1) providing an electrophoresis device; (2) adding to the device a solution mixture containing DNA fragments, a number of which are of different lengths; (3) energizing the device, thereby creating a sequence of unidirectional uniform electric field pulses therein, said sequence of field pulses alternating between primary positive voltage pulses and secondary pulses of a negative or a positive polarity with less voltage than the primary pulses; (4) calculating the time duration and the field strength required for the primary and secondary field pulses to enable resolution of the fragments into separate and distinct groups corresponding to their lengths; and (5) applying in the device the selected primary and secondary fields with intensities and durations corresponding to the size of fragments to be separated.

2. A process in accordance with claim 1 wherein the secondary pulses have a voltage of zero.

3. A process in accordance with claim 1 wherein the DNA fragments to be separated possess over 20,000 base pairs.

4. A process in accordance with claim 1 wherein the DNA fragments to be separated possess between about 2,000 and about 2,500,000 base pairs.

5. A process in accordance with claim 1 wherein the electric field pulses have a strength of between about 0.25 and about 2.5 volt/cm.

6. A process in accordance with claim 1 wherein the electric current of the field is between about 4 and about 80 milliamps.

7. A process in accordance with claim 1 wherein the solution mixture is maintained at a temperature between about 20° C. and about 25° C.

8. A process in accordance with claim 1 wherein the DNA molecules to be separated are selected from the group consisting of bacteria phage lambda, human, horse, and yeast.

9. A process in accordance with claim 1 wherein the device is an electrophoretic cell with a power supply.

10. A process in accordance with claim 1 wherein the duration of each primary field pulse is between about 10 seconds and about 1,000 seconds.

11. A process in accordance with claim 1 wherein the duration of each secondary pulse is between about 10 seconds and about 3,000 seconds.

12. A process in accordance with claim 1 wherein the duration of each secondary pulse consisting of zero field conditions is between about 10 seconds and about 3,000 seconds.

13. A process in accordance with claim 1 wherein the primary and secondary fields may have shapes selected from the group consisting of square, triangular increasing, triangular decreasing, stepwise increasing, and stepwise decreasing.

14. A process in accordance with claim 1 wherein the electrophoresis device further contains, as part of the solution mixture, a buffer solution.

15. A process in accordance with claim 14 wherein the buffer solution comprises 0.089 molar tris base, 0.089 molar boric acid, and 0.002 molar ethylenedinitrolo tetraacetic acid disodium salt.

16. A process in accordance with claim 1 wherein the solution mixture comprises a gel comprising, in addition to DNA fragments, a solvent and agarose.

17. A process in accordance with claim 16 wherein the concentration of agarose in the gel is between about 0.2 and about 2 percent by weight.

18. A process in accordance with claim 16 wherein the concentration of agarose in the gel is between about 0.3 and about 1 percent by weight.

19. A process in accordance with claim 16 wherein the pore size within the gel is between about 30 nanometers and about 300 nanometers.

20. A process in accordance with claim 16 wherein the pore size within the gel is between about 60 nanometers and about 200 nanometers.

21. A process in accordance with claim 16 wherein the fragments to be separated possess between about 5,000 and 5,000,000 base pairs, the concentration of agarose in the gel is between about 0.2 percent and about 2 percent by weight, the average pore size in the gel is between about 30 nanometers and about 300 nanometers, the primary electric field has a strength of between about +0.25 and about 2.5 volt/cm, and the electric current of the field is between about 4 and about 80 milliamperes, the temperature of the mixture is maintained between about 20° C. and about 25° C., the primary field is applied in pulses of about 10 seconds to about 1,000 seconds, and between about 10 seconds and about 3,000 seconds are allowed between each primary pulse, during which time the secondary pulses are of zero-field conditions.

22. A process in accordance with claim 16 wherein the fragments to be separated possess up to about 300,000 base pairs, the concentration of agarose in the gel is about 0.4 percent by weight, the average pore size in the gel is about 1400 Å, the primary electric field has a strength of about +1.46 volt/cm and the electric current is about 35 milliamperes, the temperature of the mixture is maintained at about 20° C., the primary field is applied in pulses of about 30 seconds, and about 90 seconds are allowed between each primary pulse, during which time the secondary pulses are of zero-field conditions.

23. A process in accordance with claim 16 wherein the fragments to be separated possess between about 5,000 and about 5,000,000 base pairs, the concentration of agarose in the gel is between about 0.2 percent and about 2 percent by weight, the average pore size in the gel is between about 30 nanometers and about 300 nanometers, the electric current is between about 4 milliamperes and about 80 milliamperes, the primary electric field is between about +0.25 and about +2.5 volt/cm, the temperature of the mixture is maintained between about 20° C. and about 25° C., the primary field is applied in pulses of between about 10 seconds and about 1,000 seconds, and between about 10 seconds and about 3,000 seconds are allowed between each primary pulse, during which time a secondary pulse of positive or negative polarity and having a strength less than that of the primary field pulses is applied.

24. A process in accordance with claim 16 wherein the fragments to be separated possess up to about 420,000 base pairs, the concentration of agarose in the gel is about 0.6 percent by weight, the average pore size in the gel is about 1200 Å, the electric current is about 40 milliamperes and the primary electric field is about +2.0 volt/cm, the temperature of the mixture is maintained at about 20° C., the primary field is applied in pulses of about 90 seconds, and about 90 seconds are allowed between each primary pulse, during which time a secondary pulse of negative polarity and having a strength of approximately −1.0 volt/cm is applied.

25. A process for enabling the separation of a mixture of DNA fragments comprising: (1) providing an electrophoresis device; (2) adding to the device a solution mixture containing DNA fragments, a number of which are of different lengths; (3) energizing the device, thereby creating a squence of unidirectional uniform electric field pulses therein, said sequence of field pulses alternating between primary positive voltage pulses and secondary pulses of negative or positive polarity with less voltage than the primary pulses; (4) calculating the time duration and the field strength required for the primary and secondary field pulses to enable resolution of the fragments into separate and distinct groups corresponding to their lengths, the step of calculating including the steps of: (a) providing approximate values for the time durations and field strengths of the primary and secondary pulses; (b) calculating the positions of each group of fragments in the gel at the end of the process; (c) providing new approximate values for the time durations and field strengths of the primary pulses and recalculating the positions of each group of fragments in the gel at the end of the process; and (d) repeating step (c) until the results of the calculations indicate that the fragment groups will be separated optimally at the end of the process; and (5) applying the primary and secondary fields with intensities and durations corresponding to the size of fragments to be separated.

26. A process for enabling the separation of a mixture of DNA fragments comprising: (1) providing an electrophoresis device; (2) adding to the device a solution mixture containing DNA fragments, a number of which are of different lengths; (3) energizing the device, thereby creating a sequence of unidirectional uniform electric field pulses therein, said sequence of field pulses alternating between primary positive voltage pulses and secondary pulses of negative or positive polarity, and of lesser voltage than the primary pulses; (4) calculating the time duration and the intensity required for the primary and secondary field pulses to enable resolution of the fragments into separate and distinct groups corresponding to their lengths, the step of calculating including: (a) defining: (i) the DNA fragment size; (ii) the density of agarose in a gel contained in the electrophoresis device; (iii) the persistence length of DNA; (iv) the temperature within the device; (v) the viscosity of a buffer solution contained in the electrophoresis device; and (vi) the screening effect of the cations in the solution that lowers the number of net charges available on a DNA molecule; (b) providing approximate values for: (i) the time durations of the primary and secondary pulses; and (ii) the intensity and polarity of the electric field during the primary and secondary pulses; (c) calculating the velocity of each group of fragments contained in the mixture during the electrophoresis process; (d) calculating the position of each group of fragments in the gel after an process of given duration; (e) calculating the width of each group of DNA fragments of a given molecular weight in the gel; and (f) repeating steps (c) through (e), each time providing new values for the time durations of the primary and secondary pulses and providing new values for the intensity and polarity of the electric field during the primary and secondary pulses until the results of steps (c) through (e) indicate that these values have been chosen to provide optimal separation of the DNA fragments; and (5) applying the primary and secondary fields with intensities and durations corresponding to the size of fragments to be separated.

27. A process in accordance with claim 26 wherein the secondary pulses have a voltage of zero.

28. A process in accordance with claim 26 wherein the step of calculating includes: (a) specifying the number of segments forming a DNA molecule; (b) specifying the number of DNA molecules present in the solution mixture; (c) specifying the duration of the electrophoretic separation to be performed; (d) specifying the pore size within the gel; and (e) specifying a solvent friction coefficient by specifying the mobility of a DNA molecule in a solution containing no agarose.

29. A process in accordance with claim wherein the step of calculating includes (a) selecting a first variable from the group consisting of: (i) the field applied during the primary pulse; (ii) the field applied during the secondary pulse; (iii) the duration of the first pulse; (iv) the duration of the second pulse; (v) the number of segments forming a DNA molecule; (vi) the number of DNA molecules present in the solution mixture; (vii) the duration of the electrophoretic separation to be performed; (viii) the pore size of the gel; (ix) the persistence length of DNA molecules; (x) the temperature within the device; (xi) the mobility of a DNA molecule in a solution containing no agarose; and (xii) the screening effect of the cations in solution that lowers the net number of negative charges available on a molecule; and (b) entering a random number for the variable for the purpose of simulating a DNA gel electrophoresis process.

30. A process in accordance with claim 29 wherein the step of calculating includes choosing a second variable from the group consisting of: (i) the field applied during the primary pulse; (ii) the field applied during the secondary pulse; (iii) the duration of the first pulse; (iv) the duration of the second pulse; (v) the number of segments forming a DNA molecule; (vi) the number of DNA molecules present in the solution mixture; (vii) the duration of the electrophoretic separation to be performed; (viii) the pore size of the gel; (ix) the persistence length of DNA molecules; (x) the temperature within the device; (xi) the mobility of a DNA molecule in a solution containing no agarose; and (xii) the screening effect of the cations in solution that lowers the net number of negative charges available on a molecule; and which second variable may be any member of the group except for the variable selected as the first variable.

31. A process in accordance with claim 30 wherein the step of calculating includes providing constant values for all members of the group other than those chosen as the first and second variables.

32. A process in accordance with claim 31 wherein the step of calculating includes determing the value of the effective charge on each DNA segment, determining the value of the angle of an end segment of a DNA fragment with respect to the electric field, determining the displacement of a given DNA fragment, and calculating the characteristic streching time for a DNA chain.

33. A process in accordance with claim 16 wherein the gel used is agarose NA.

* * * * *

UNITED STATES PATENT AND TRADEMARK OFFICE

CERTIFICATE OF CORRECTION

PATENT NO. : 4,971,671

DATED : November 20, 1990

INVENTOR(S) : Gary W. Slater and Jaan Noolandi

It is certified that error appears in the above-identified patent and that said Letters Patent is hereby corrected as shown below:

In column 7, line 15, the formula should appear as follows:

$$\frac{E_p}{E_s} \gg \frac{T_s}{T_p}$$

Signed and Sealed this

Twenty-first Day of April, 1992

*Attest:*

HARRY F. MANBECK, JR.

*Attesting Officer*

*Commissioner of Patents and Trademarks*